United States Patent
Suzuki et al.

(10) Patent No.: US 9,782,304 B2
(45) Date of Patent: Oct. 10, 2017

(54) ABSORBENT ARTICLE WITH NEW LEG GATHERS

(75) Inventors: Migaku Suzuki, Chigasaki (JP); Yoshio Hirai, Tokyo (JP)

(73) Assignee: DAIO PAPER CORPORATION, Shikokuchuo-Shi (JP)

( * ) Notice: Subject to any disclaimer, the term of this patent is extended or adjusted under 35 U.S.C. 154(b) by 0 days.

(21) Appl. No.: 14/422,295

(22) PCT Filed: Aug. 20, 2012

(86) PCT No.: PCT/JP2012/070991
§ 371 (c)(1),
(2), (4) Date: Feb. 18, 2015

(87) PCT Pub. No.: WO2014/030200
PCT Pub. Date: Feb. 27, 2014

(65) Prior Publication Data
US 2015/0190289 A1 Jul. 9, 2015

(51) Int. Cl.
*A61F 13/15* (2006.01)
*A61F 13/49* (2006.01)
(Continued)

(52) U.S. Cl.
CPC .. *A61F 13/49015* (2013.01); *A61F 13/49413* (2013.01); *A61F 13/5638* (2013.01);
(Continued)

(58) Field of Classification Search
CPC .......... A61F 13/49015; A61F 13/49413; A61F 13/5638; A61F 13/537; A61F 2013/49042; A61F 2013/49433
(Continued)

(56) References Cited

U.S. PATENT DOCUMENTS 4,808,177 A * 2/1989 DesMarais ........ A61F 13/49017
604/385.27
5,397,318 A * 3/1995 Dreier ............... A61F 13/49009
604/385.19
(Continued)

FOREIGN PATENT DOCUMENTS

EP    1 982 679 A1   10/2008
EP    2 815 732 A1   12/2014
(Continued)

OTHER PUBLICATIONS

Nov. 20, 2012 International Search Report issued in International Application No. PCT/JP2012/070991.
(Continued)

*Primary Examiner* — Jacqueline Stephens
(74) *Attorney, Agent, or Firm* — Oliff PLC

(57) ABSTRACT

An absorbent article includes: a sheet-type leakage-preventing body; absorbent body, at least one layer arranged on the leakage-preventing body top, which absorb fluids; pair of left and right floating leg gathers on the absorbent body top, extending in longitudinal direction from the main body front end of the absorbent article to the rear end, traversing a front body section, crotch part, and rear body section. Each floating leg gathers have a top and trailing parts adjoining the top part. Front and rear ends of the floating leg gathers are joined respectively to the vicinity of the front and rear end of the absorbent article main body. Trailing parts trail downwards from top parts towards the absorbent body. At least one part of the trailing parts of the left and right floating leg gathers is mutually connected in the lower end area forming a channel for bodily fluids inside trailing parts.

26 Claims, 15 Drawing Sheets

(51) Int. Cl.
  *A61F 13/494*    (2006.01)
  *A61F 13/56*     (2006.01)
  *A61F 13/537*    (2006.01)

(52) U.S. Cl.
  CPC ... *A61F 13/537* (2013.01); *A61F 2013/49092* (2013.01); *A61F 2013/49433* (2013.01)

(58) Field of Classification Search
  USPC .......................... 604/385.28, 385.25, 385.24
  See application file for complete search history.

(56) References Cited

U.S. PATENT DOCUMENTS

| | | | |
|---|---|---|---|
| 5,558,660 A * | 9/1996 | Dreier ................... | A61F 13/495 604/378 |
| H001630 H * | 1/1997 | Roe ................... | A61F 13/49413 604/385.28 |
| 2004/0002690 A1 | 1/2004 | Miyamoto | |
| 2005/0267436 A1 | 12/2005 | Mishima et al. | |
| 2007/0088306 A1 | 4/2007 | Sugiyama et al. | |
| 2007/0149943 A1 * | 6/2007 | Miyamoto ........ | A61F 13/49413 604/385.28 |
| 2009/0036852 A1 | 2/2009 | Suzuki et al. | |

FOREIGN PATENT DOCUMENTS

| | | |
|---|---|---|
| JP | H03-234257 A | 10/1991 |
| JP | 3234257 B2 | 12/2001 |
| JP | 2005334537 A | 12/2005 |
| JP | 2009017929 A | 1/2009 |

OTHER PUBLICATIONS

Dec. 18, 2012 Office Action issued in Japanese Application No. 2012-538116.
Nov. 20, 2012 Written Opinion of the International Searching Authority issued in International Application No. PCT/JP2012/070991.
Dated Apr. 5, 2016 Extended European Search Report issued in European Patent Appliction No. 12883414.0.

* cited by examiner (A)

(B)

(A)

(B)

(C)

(D)

(E)

(A)

(B)

(C)

(D)

(E)

ABSORBENT ARTICLE WITH NEW LEG GATHERS

FIELD OF THE INVENTION

The present invention relates to an absorbent article with new leg gathers.

BACKGROUND ART

Absorbent articles such as paper diapers (for infants and adults), sanitary napkins, incontinence articles, training pants or the like are articles that absorb bodily fluids, such as urine excreted from a wearer, by means of an absorber that makes use of a super absorbent polymer (hereinafter referred to as an "SAP"), fluffy pulp or the like.

Conventional absorbent articles prevent leakage by closely attaching an absorber to the surface of the body of a wearer without any gap and by transferring the excreted bodily fluids from the surface of the absorber to the inside thereof to be absorbed therein.

Such closely-attached state of the absorber to the body of the wearer is achieved by applying a "pressing force from the exterior" to the absorber. This will be described in more detail by taking an infant's diaper as an example.

For infant's diapers, in diapers where a "pressing force from the exterior" occurs, various stretchable materials (similar to those used in pantyhose, supporters, competition swimsuits and the like) are arranged at various parts. Especially in recent years, for tapeless underpants-type diapers which have become a main trend for infant' diapers, since they are mainly intended for infants when their body movement becomes active (approximately 6 kg or more in body weight), it is necessary to make use of a stretchable material.

In general, the following stretchable materials are used for underpants-type diapers:

(1) A waist gather band (waist part stretchable body): the waist gather band serves as a fixing band that connects a front end part and a rear end part of a diaper body to each other, attaches the diaper closely around the waist and prevents the diaper from sliding down;

(2) Shining gathers or trunk gathers (trunk part maintaining stretchable body): the shining or trunk gathers are present so as to cover each of a back surface and a ventral surface of the diaper and exhibit functions of pressing the absorber in the vicinity of the back surface and in the vicinity of the ventral surface against the surface of the wearer's body; and (3) Leg gathers (leg part stretchable body): the leg gathers provide sealing, in the vicinity of the crotch part, so that no gap is formed between the diaper body and the wearer's body and play a role of a dam (bank) that prevents leakage from the side surfaces of the absorber. The leg gathers are classified into the following three types depending on their roles, and each type may be used alone or two or more types may be used in combination.

(3a) First inner leg gather (ILG): the first ILG is provided above the absorber or on a side edge of the absorber, includes a stretchable head part and a leg part made of a non-woven fabric, and usually has a standing geometry.

(3b) Second inner leg gather (ILG): the second ILG is provided on the side edge of the absorber or on the exterior thereof, includes a stretchable head part and a leg part made of a non-woven fabric and usually has a standing geometry.

(3c) Outer leg gather (OLG) or gusset gather: the OLG or gusset gather is provided by sandwiching a stretchable material by a top sheet and a leak preventer from both surfaces at the side edge of the diaper body, and it is usually flat; however, it is folded on the inward side, in some cases, to be used in a standing geometry.

SUMMARY OF THE INVENTION

Problems to be Solved by the Invention

When the above-described stretchable materials are used in a form where a strong tension concentrates, as in a wide rubber band, they give the wearer a feeling of restraint and leave marks, and thus, in general, improvement efforts have been made such as to arrange a plurality of fine polyurethane filaments in parallel to disperse tension. However, current diapers are still greatly associated with a feeling of restraint for the wearer, both physically and psychologically.

In addition, since conventional diapers achieve the closely-attached state of the absorber to the wearer's body by a "pressing force from the exterior," hot and stuffy state and rashes are likely to occur.

Accordingly, it is an object of the present invention to provide an absorbent article that has less of a feeling of restraint at the time of wearing and in which the occurrence of hot and stuffy state and rashes is suppressed.

Means for Solving the Problems

In order to achieve the object set forth above, the present inventors contemplated achieving an absorbent article that has less of a feeling of restraint at the time of wearing and in which the occurrence of hot and stuffy state and rashes is suppressed, by means of a new concept, without using a "pressing force from the exterior."

As a result of diligently conducting research, the present inventors have found that: by providing a pair of right and left floating leg gathers (hereinafter referred to as an "FLG"), which includes a head part and a hanging part that connects to the head part and which is configured such that a front end part and a rear end part of the FLG are respectively coupled to the vicinity of a front end part and the vicinity of a rear end part of the absorbent article body and such that the hanging part hangs down from the head part toward the absorber, as a pair of FLGs arranged, above the absorber, from a front end part to a rear end part of the absorbent article body in the length direction via a front body, a crotch part and a rear body; and by connecting at least parts of the hanging parts of the pair of right and left FLGs to each other in the vicinity of the lower end parts thereof so as to form a transferring passage for bodily fluids on the inner surface sides of the hanging parts, the FLGs and the absorber are spaced apart at the time of wearing the absorbent article, and thus, a feeling of restraint at the time of wearing is reduced and contact of the urine or feces excreted onto the absorber with the wearer's skin is effectively suppressed and thus, the occurrence of hot and stuffy state and rashes is suppressed, and then completed the present invention.

The present invention focuses especially on a skin contact member and an absorber member, among the members configuring the absorbent article.

(1) In the conventional absorbent article, both the absorber and the gather that stands up therefrom are pressed against the wearer's skin, whereas in the present invention, a "skin contact member which functions by being constantly and closely attached in a soft manner to the skin of the wearer on the side edges of the bodily fluid excretory organ"

and an "absorber member which is rigid and requires a form retaining property" are functionally separated.

(2) The above-described "absorber member" is physically spaced apart from the surface of the wearer's body.

(3) In regard to the above-described "skin contact member," a pair of FLGs having a pair of right and left head parts and a pair of right and left hanging parts that hangs down from the head parts toward the absorber member, are provided as a separate entity.

Based on the above, the present invention is to provide a new absorbent article in which the absorber is not pressed against the wearer's body surface like in the conventional absorbent article and which is capable of sufficiently fulfilling the absorption function of the absorber while keeping the absorber spaced apart from the wearer's body surface.

Namely, the present invention provides the following (1) to (24):

(1) An absorbent article including:

a leak preventer in sheet form;

an absorber capable of absorbing a bodily fluid, wherein at least one layer thereof is arranged above the leak preventer; and a pair of right and left floating leg gathers that are arranged, above the absorber, from a front end part to a rear end part in a length direction of a body of the absorbent article via a front body, a crotch part and a rear body;

wherein the floating leg gather has a head part and a hanging part that connects to the head part, wherein a front end part and a rear end part of the floating leg gather respectively couple to the vicinity of the front end part and the rear end part of the body of the absorbent article, the hanging part being configured to hang down from the head part toward the absorber, and wherein at least parts of the hanging parts of the pair of right and left floating leg gathers are connected to each other in the vicinity of lower end parts thereof so as to form a transferring passage for bodily fluids on inner surface sides of the hanging parts.

(2) The absorbent article according to (1), wherein an upper part of the transferring passage for bodily fluids is open.

(3) The absorbent article according to (1) or (2), wherein, for each of the pair of right and left floating leg gathers, the head part is arranged to face outward and the hanging part is arranged to face inward, and the hanging parts of the pair of right and left floating leg gathers are connected to each other by being respectively coupled to a connection sheet at the lower end parts thereof.

(4) The absorbent article according to (3), wherein each of outer surfaces of the hanging parts of the pair of right and left floating leg gathers and the connection sheet are coupled.

(5) The absorbent article according to (3), wherein each of inner surfaces of the hanging parts of the pair of the right and left floating leg gathers and the connection sheet is coupled.

(6) The absorbent article according to any one of (3) to (5), wherein a length in the front-rear direction of the connection sheet is longer than a width in the lateral direction of the connection sheet.

(7) The absorbent article according to any one of (3) to (5), wherein a length in the front-rear direction of the connection sheet is equal to or less than a width in the lateral direction of the connection sheet.

(8) The absorbent article according to any one of (3) to (7), wherein a width in the lateral direction of the connection sheet narrows down from a front side to a rear side.

(9) The absorbent article according to any one of (3) to (8), wherein right and left edge parts of the connection sheet are folded back inwardly on an upper side.

(10) The absorbent article according to any one of (3) to (8), wherein right and left edge parts of the connection sheet are folded back inwardly on an upper side and the inwardly-folded-back parts are further folded back outwardly.

(11) The absorbent article according to any one of (3) to (10), wherein the connection sheet is configured by a hydrophilic material.

(12) The absorbent article according to any one of (3) to (10), wherein the connection sheet is configured by a hydrophobic material.

(13) The absorbent article according to any one of (3) to (10), wherein the connection sheet is configured by a combination of a hydrophilic material and a hydrophobic material.

(14) The absorbent article according to any one of (3) to (10), wherein the connection sheet is configured by a material in which hydrophilicity and hydrophobicity are compounded.

(15) The absorbent article according to any one of (3) to (17), wherein the connection sheet is provided beyond a front end and/or a rear end of parts of the hanging parts of the pair of right and left floating leg gathers, which form the transferring passage for bodily fluids.

(16) The absorbent article according to (1) or (2), wherein, for each of the pair of right and left floating leg gathers, the head part is arranged to face outward and the hanging part is arranged to face inward; and the hanging parts of the pair of right and left floating leg gathers are connected to each other by being respectively directly coupled to each other in the vicinity of the lower end parts thereof.

(17) The absorbent article according to any one of (1) to (16), wherein a member configuring the transferring passage for bodily fluids and a surface of the absorber are spaced apart.

(18) The absorbent article according to any one of (1) to (16), wherein a member configuring the transferring passage for bodily fluids and surface of the absorber are coupled to each other.

(19) The absorbent article according to (18), wherein a member configuring the transferring passage for bodily fluids couples to a surface of the absorber in the vicinity of a front end and/or a rear end of the transferring passage for bodily fluids, whereby a height of the transferring passage for bodily fluids is low at a fixed part and high at a non-fixed part.

(20) The absorbent article according to any one of (3) to (19), wherein a transferring direction of the bodily fluid is defined by the transferring passage for bodily fluids having a height difference in the front-rear direction.

(21) The absorbent article according to (20), wherein the height difference in the transferring passage for bodily fluids is provided due to the existence of a plurality of positions in the vertical direction for coupling the hanging parts of the pair of right and left floating leg gathers to the connection sheet, along the front-rear direction.

(22) The absorbent article according to any one of (1) to (21), wherein the transferring passage for bodily fluids is provided at least in a region of a crotch part.

(23) The absorbent article according to any one of (1) to (22), wherein the transferring passage for bodily fluids is provided at least in a region of a front body.

(24) The absorbent article according to any one of (1) to (23), wherein the transferring passage for bodily fluids is provided at least in a region of a rear body.

Effect of the Invention

An absorbent article according to the present invention has a less of a feeling of restraint at the time of wearing and in which the occurrence of hot and stuffy state and rashes is suppressed.

BRIEF DESCRIPTIONS OF THE DRAWINGS

FIG. 1 contains schematic diagrams illustrating the principles of forming a "transferring passage for bodily fluids" by means of self-connected type FLGs.

FIG. 2 contains schematic diagrams illustrating an example of an absorbent article according to the present invention.

Figure 5:
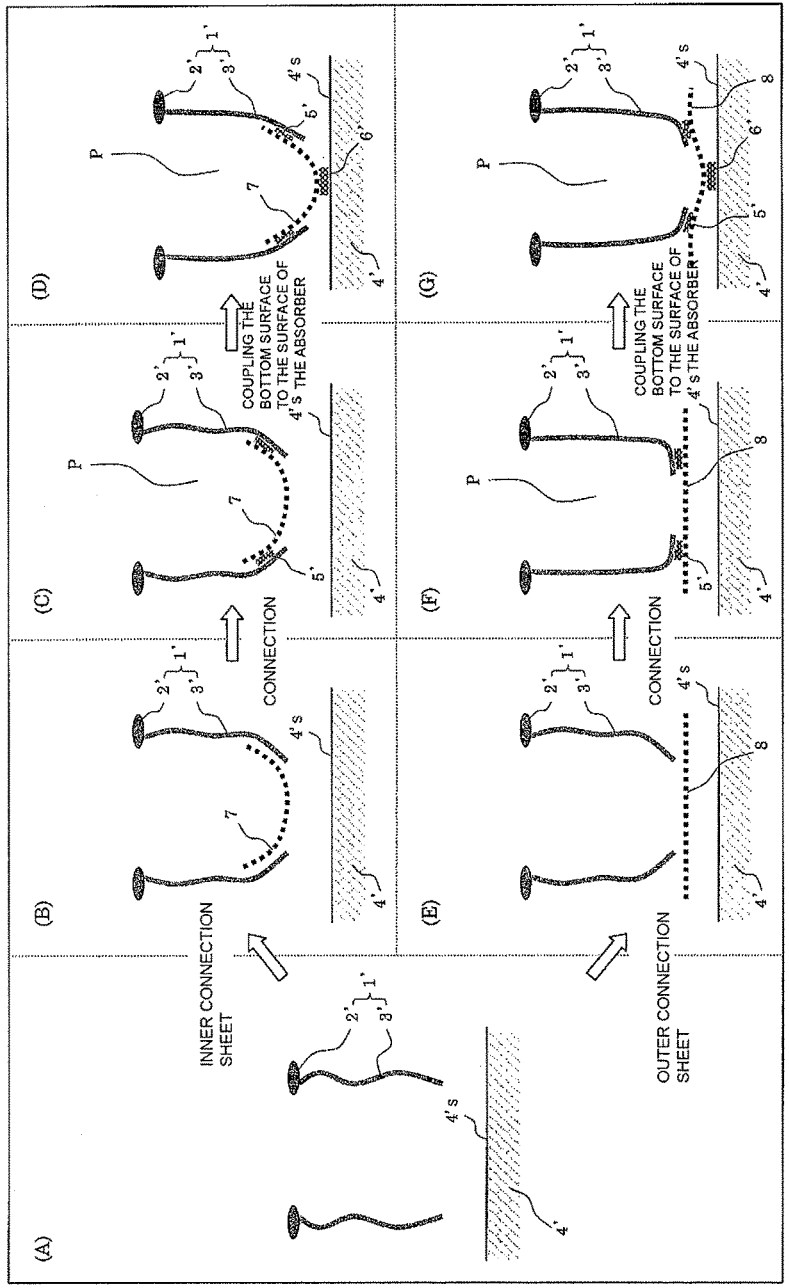

FIG. 5 contains schematic diagrams illustrating the principles of forming a "transferring passage for bodily fluids" by means of connection sheet type FLGs.

Figure 6:
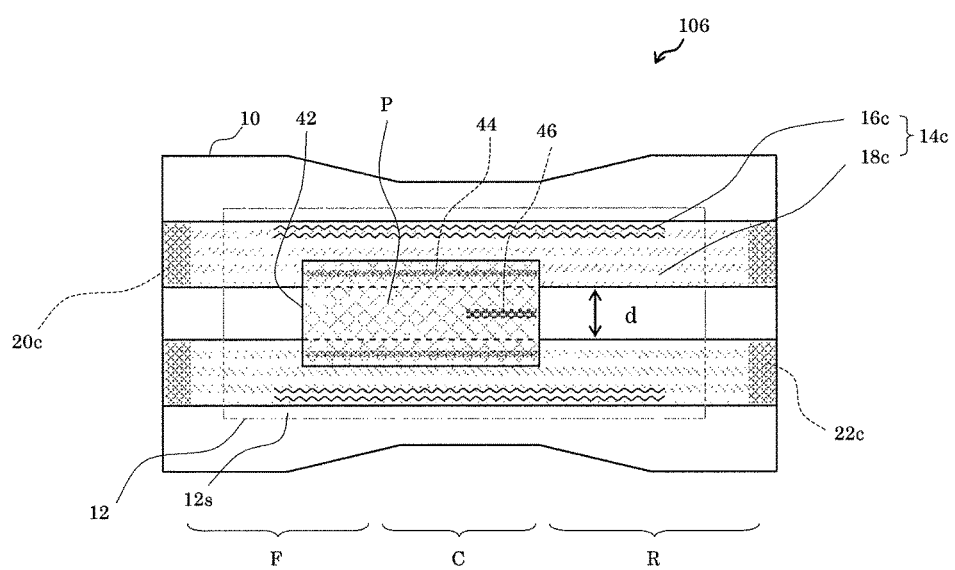

FIG. 6 is a schematic developed plan view illustrating another example of the absorbent article according to the present invention.

Figure 7:
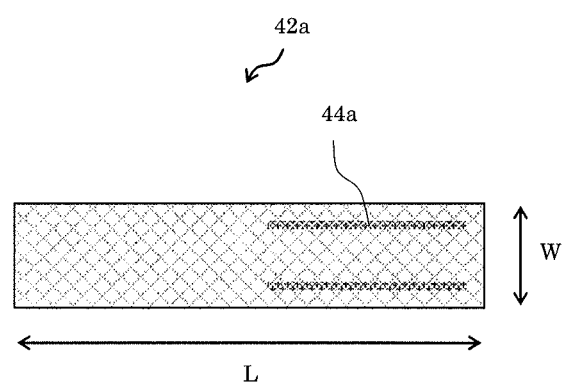
Figure 7:
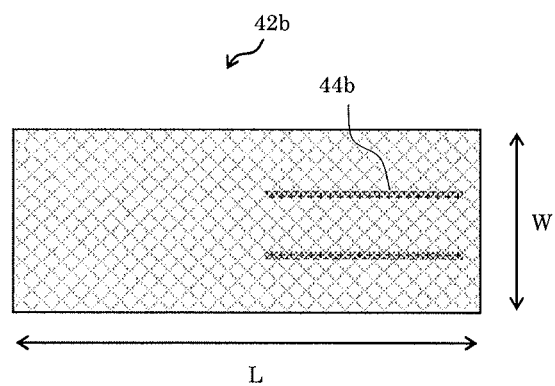
Figure 7:
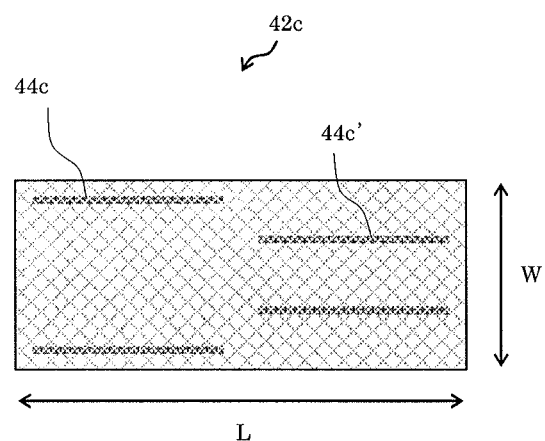
Figure 7:
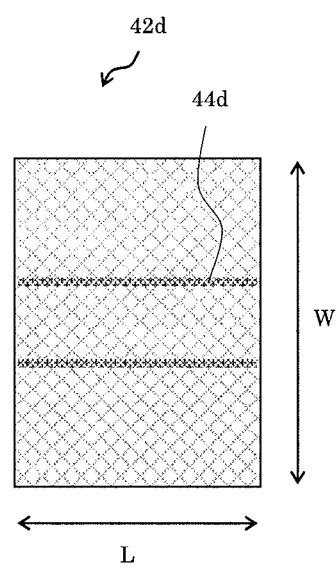
Figure 7:
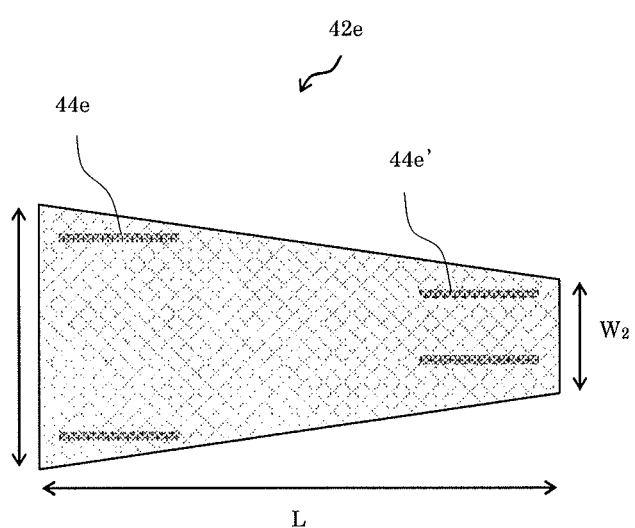

FIG. 7 contains schematic diagrams illustrating various connection sheets.

Figure 8:
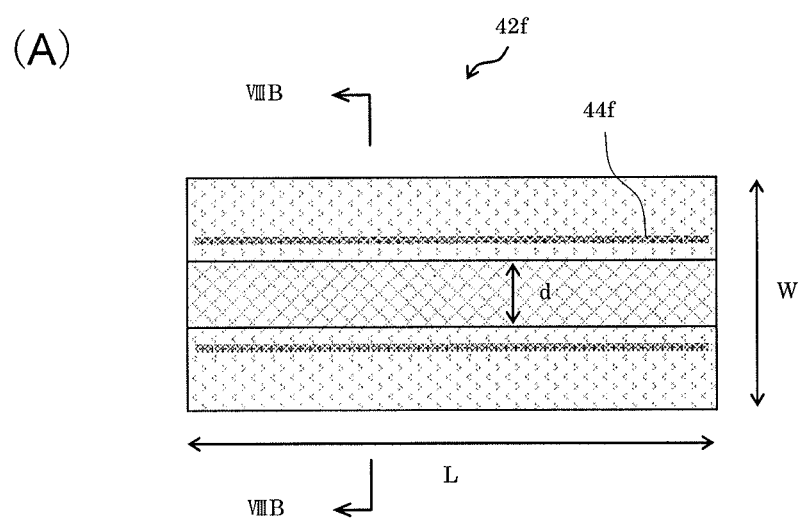
Figure 8:
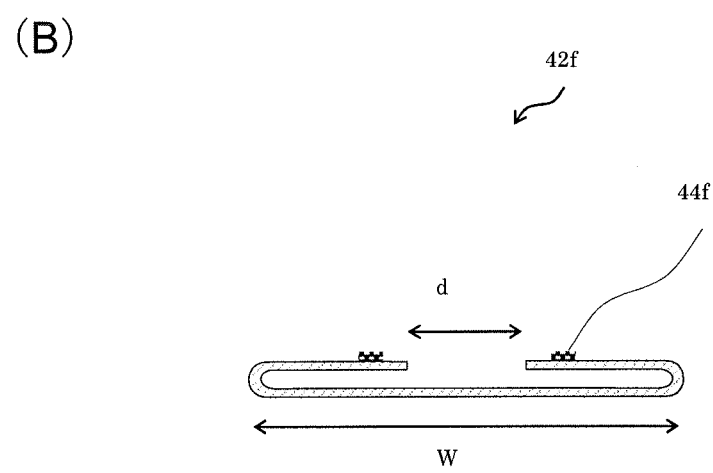
Figure 8:
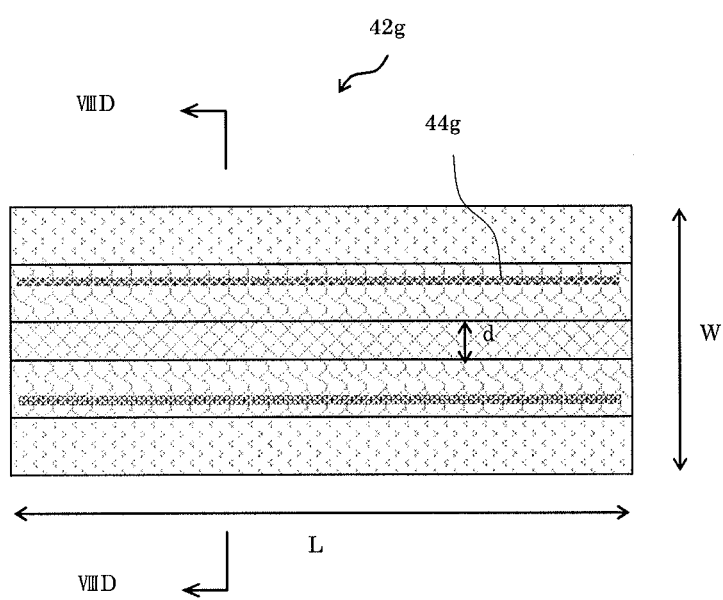
Figure 8:
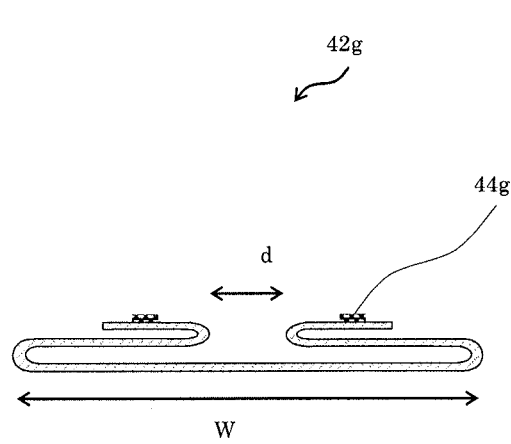
Figure 8:
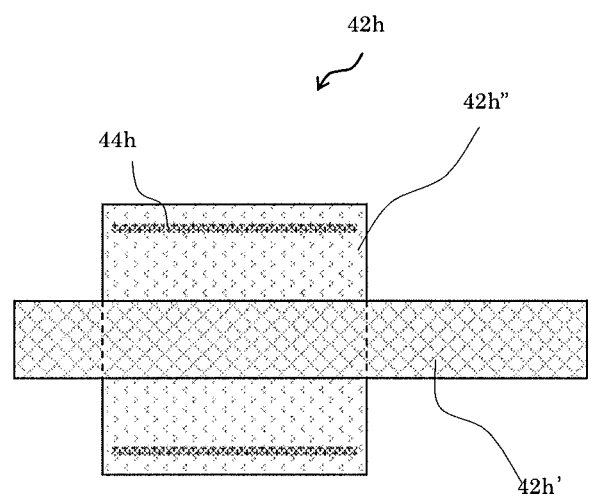

FIG. 8 contains schematic diagrams illustrating various connection sheets.

Figure 9:
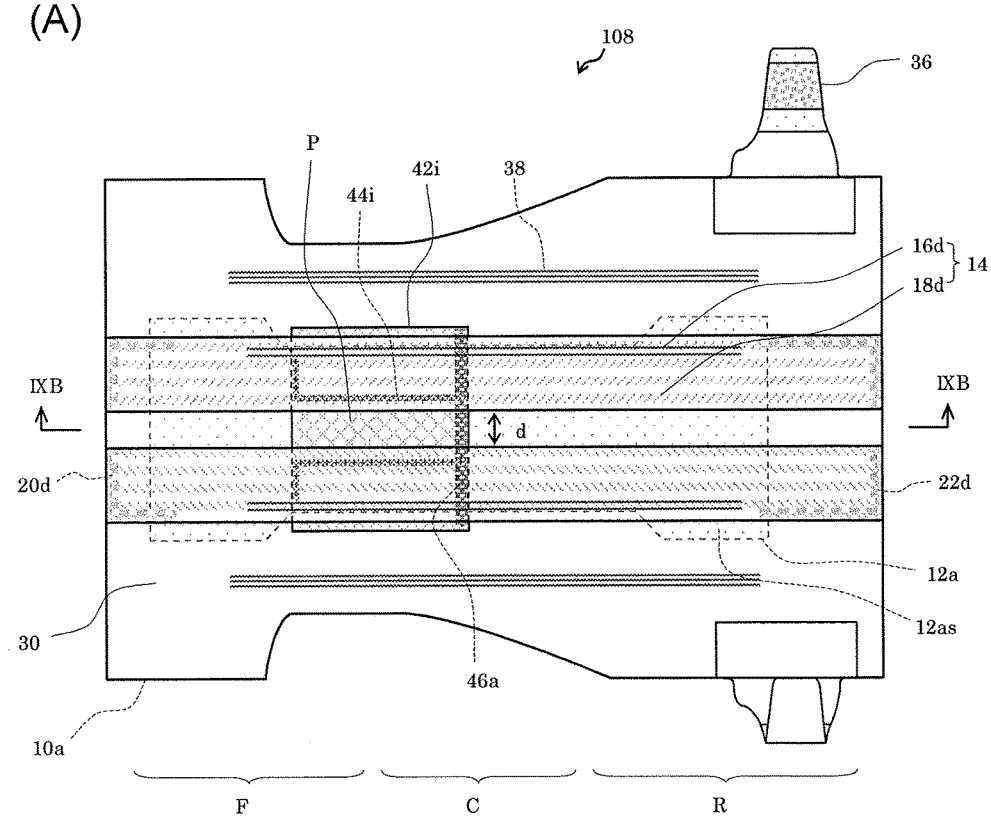
Figure 9:
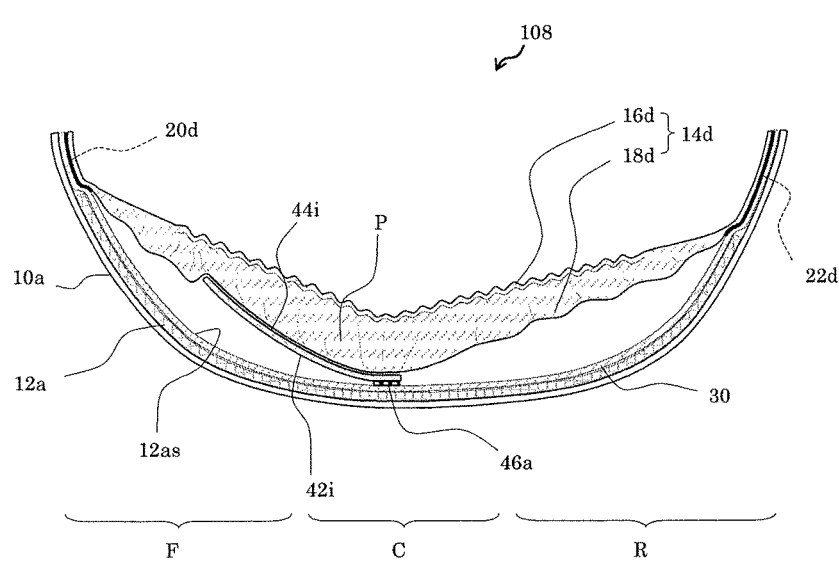

FIG. 9 contains schematic diagrams illustrating a further embodiment of the absorbent article according to the present invention.

Figure 10:
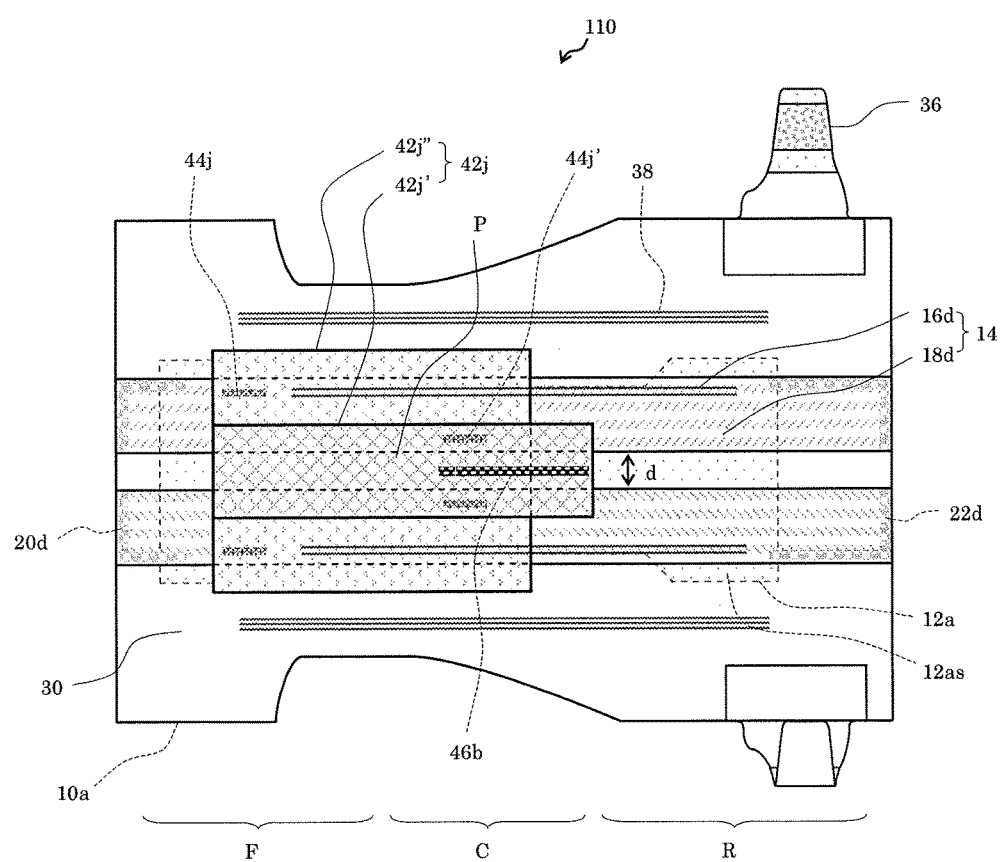

FIG. 10 is a schematic developed plan view illustrating a further example of the absorbent article according to the present invention.

Figure 11:
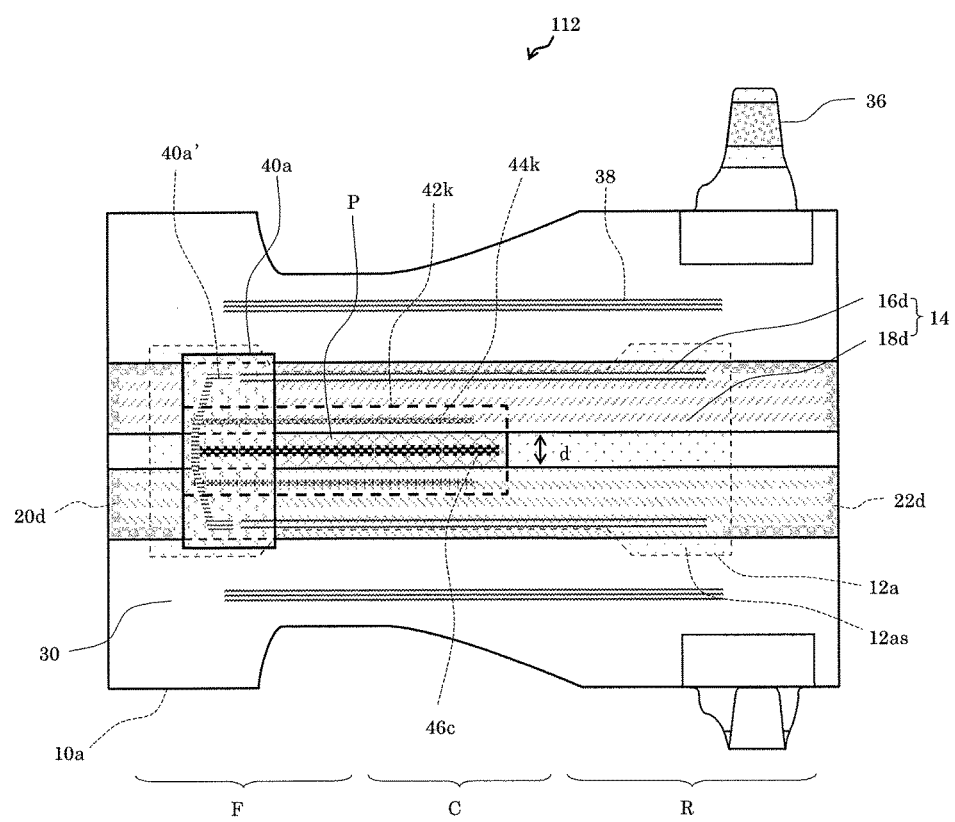

FIG. 11 is a schematic developed plan view illustrating a further example of the absorbent article according to the present invention.

EMBODIMENTS OF THE INVENTION

Hereinafter, the absorbent article according to the present invention will be described in detail, based on the preferred embodiments illustrated in the attached drawings. It should be noted that, in the present specification, when the absorbent article according to the present invention is actually worn, a side close to the skin of the wearer will be referred to as the "top" and a side far therefrom will be referred to as the "bottom/under." In addition, when the absorbent article according to the present invention is actually worn, a side corresponding to the front side of the wearer's body will be referred to as the "front" and a side corresponding to the back side thereof will be referred to as the "rear." Moreover, in order to facilitate understanding, in the respective drawings, members that are actually in contact with each other may be illustrated such that they are spaced apart. In the respective plan views among the attached drawings, the front side of the absorbent article, etc. is illustrated such that it is positioned on the left side of the corresponding drawing. In the respective longitudinal end views and longitudinal sectional views among the attached drawings, the front side of the absorbent article, etc. is illustrated such that it is positioned on the left side of the corresponding drawing.

In addition, in the present specification, an "absorbent article body" collectively refers to a leak preventer, a top sheet that can be provided above the leak preventer and various other members that can be provided to the absorbent article, all of which are constituent members of the absorbent article. In accordance with this, when the absorbent article is a diaper, the absorbent article body will be referred to as a diaper body.

Moreover, in the present specification, an "absorber surface" refers to a surface of an absorber when it is exposed, and to a surface of a diffusion sheet, acquisition sheet, top sheet or the like when the absorber is covered with such diffusion sheet, acquisition sheet, top sheet or the like.

First, the fundamental principles of an FLG used in the absorbent article according to the present invention and of a transferring passage for bodily fluids formed by the FLGs will be described.

There are basically two forms in which the FLGs form a shifting passage for bodily fluids.

The first form is a form in which the hanging parts of a pair of right and left FLGs are connected to each other by being respectively directly coupled to each other in the vicinity of the lower ends thereof (i.e. a self-connected type).

The second form is a form in which the hanging parts of a pair of right and left FLGs are connected to each other by being respectively coupled to a connection sheet in the vicinity of the lower ends thereof (i.e. a connection sheet type).

Hereinafter, a description will be provided by taking a self-connected type FLG as an example.

Figure 1:
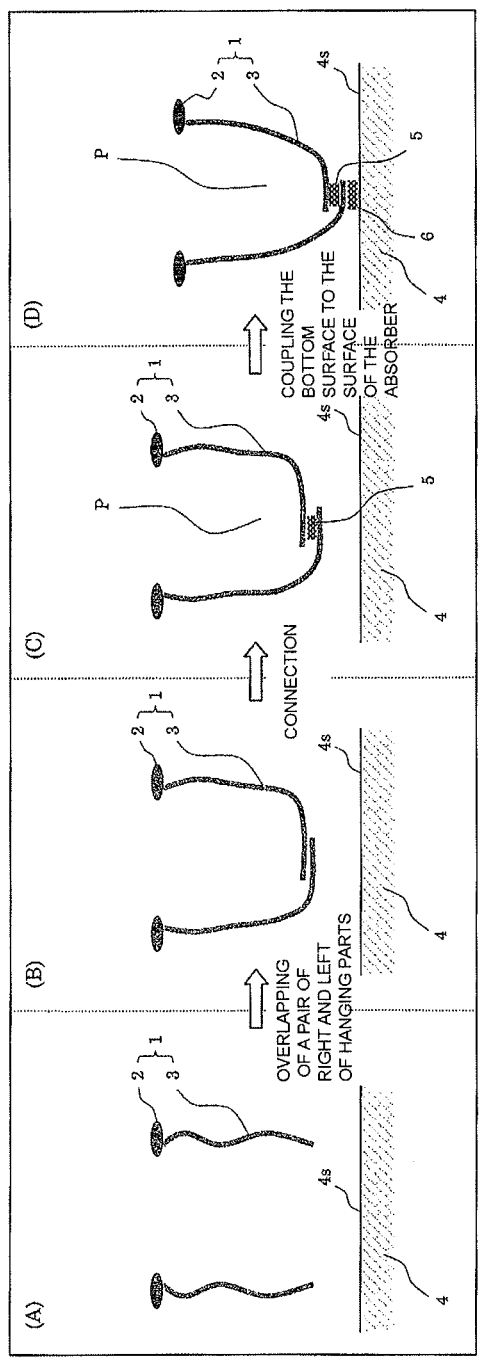

FIG. 1 contains schematic diagrams illustrating the principles of forming a "transferring passage for bodily fluids" by self-connected type FLGs. FIG. 1 only shows FLGs and an absorber of the absorbent article according to the present invention in a lateral end view.

FIG. 1(A) shows a state prior to a pair of right and left FLGs 1 being connected to each other. The pair of right and left FLGs 1 include head parts 2 and hanging parts 3 that connect to head parts 2. A front end part and a rear end part of FLG 1 are respectively coupled to the vicinity of a front end part and the vicinity of a rear end part of the absorbent article body (not shown), and hanging part 3 is configured to hang down from head part 2 toward absorber 4.

As illustrated, FLGs 1 are present in a state (i.e. a floating state) in which a pair of right and left head parts 2 and hanging parts 3 hanging down from head parts 2 are floating from surface 4s of absorber 4. In this way, despite the fact that the head parts of the FLGs of the absorbent article according to the present invention are strongly and closely attached to the wearer's body, a feeling of restraint at the time of wearing is reduced.

FIG. 1(B) shows a state in which, in order to allow the pair of right and left FLGs 1 to be connected to each other, a pair of right and left hanging parts 3 overlap with each other in the vicinity of the lower end parts thereof.

FIG. 1(C) shows a state in which the pair of right and left hanging parts 3 are connected to each other by being directly connected to each other at connection part 5 in the vicinity of the lower end parts thereof. In this way, transferring passage P for bodily fluids is formed on the inner surface sides of hanging parts 3. Since the pair of right and left head parts 2 are spaced apart, the upper part of transferring passage P for bodily fluids is open.

In this state, head part 2 is arranged to face outward and hanging part 3 is arranged to face inward. The coupling of the pair of right and left hanging parts 3 is sufficient when it is made at least part of the FLGs extending in the front-rear direction. Transferring passage P for bodily fluids is formed at this coupled part. The method of coupling the pair of right and left hanging parts 3 is not particularly limited, and the coupling may be made using, for example, a hot melt adhesive, a heated seal adhesive or the like.

FIG. 1(D) shows a state in which a member configuring transferring passage P for bodily fluids (here, hanging parts 3 of FLGs 1) couples to surface 4s of absorber 4 at coupling part 6. The method of coupling the member configuring transferring passage P for bodily fluids to surface 4s of absorber 4 is not particularly limited, and the coupling may be made using, for example, a hot melt adhesive, a heated seal adhesive or the like.

In this way, the member configuring the transferring passage for bodily fluids may either be coupled to the surface of the absorber or spaced apart from the surface of the absorber.

In the case of self-connected type, the state of existence of the FLGs is not particularly limited and various states of existence can be employed for the FLGs as long as at least parts of the hanging parts of the pair of right and left FLGs are coupled to each other by being directly coupled to each other in the vicinity of the lower end parts so as to form a transferring passage for bodily fluids on the inner surface sides of the hanging parts.

More specifically, out of (1) a form in which the hanging parts of the FLGs are not connected to each other and are present in a floating state (see FIG. 1 (A)), (2) a form in which the pair of right and left hanging parts are connected to each other so as to form a transferring passage for bodily fluids and in which members configuring the transferring passage for bodily fluids are present in a floating state (see FIGS. 1 (C)) and (3) a form in which the pair of right and left hanging parts are connected to each other so as to form a transferring passage for bodily fluids and in which members configuring the transferring passage for bodily fluids are present by being coupled to a surface of the absorber (see FIG. 1(D)), it is possible to use one type or two or more types of forms, including (2) and/or (3) in combination. In particular, preferable forms include: a form in which only form (2) is used; a form in which only form (3) is used; a form in which forms (2) and (3) are used in combination; a form in which forms (2) and (1) are used in combination; a form in which forms (3) and (1) are used in combination; and a form in which forms (2), (3) and (1) are used in combination. Of these, a form in which forms (2) and (1) are used in combination, a form in which forms (3) and (1) are used in combination, and a form in which forms (2), (3) and (1) are used in combination are preferable.

At which position in the front-rear direction this state of existence of the FLGs is provided and how the combination is made when two or more types of forms are to be combined are the key points in designing the absorbent article.

When the transferring passage for bodily fluids is provided at least in the area of the crotch part, the transferring passage for bodily fluids is located directly below the excretory organ for urine (i.e. the meatus urethra), and thus, the reception of urine is facilitated.

When the transferring passage for bodily fluids is provided at least in the area of the front body, it can be used as a passage for transferring the urine from the front to the rear.

When the transferring passage for bodily fluids is provided at least in the area of the rear body, the transferring passage for bodily fluids is located at a location close to the excretory organ for feces (i.e. the anus), and thus, the reception of feces is facilitated.

Figure 2:
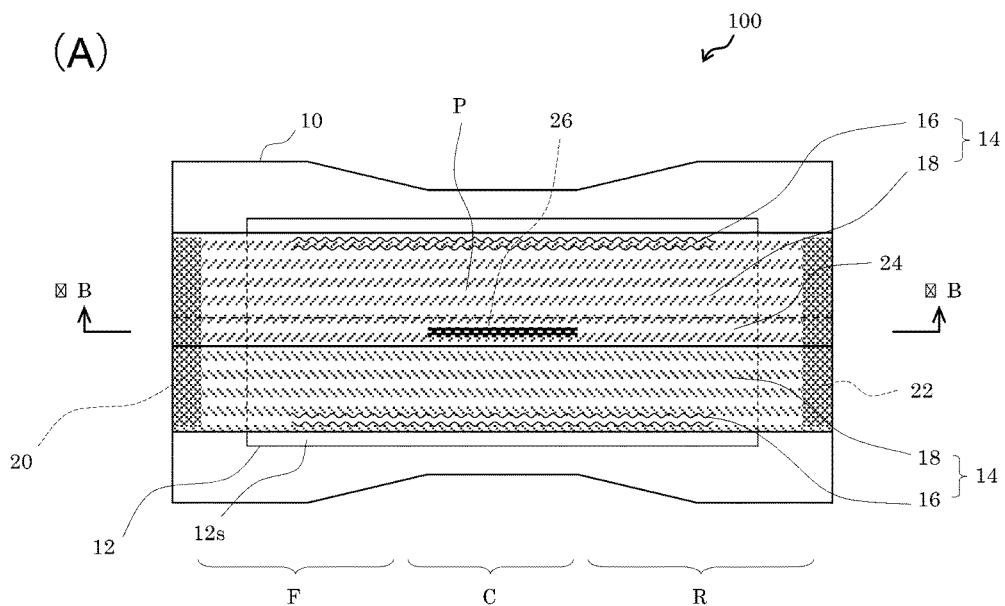
Figure 2:
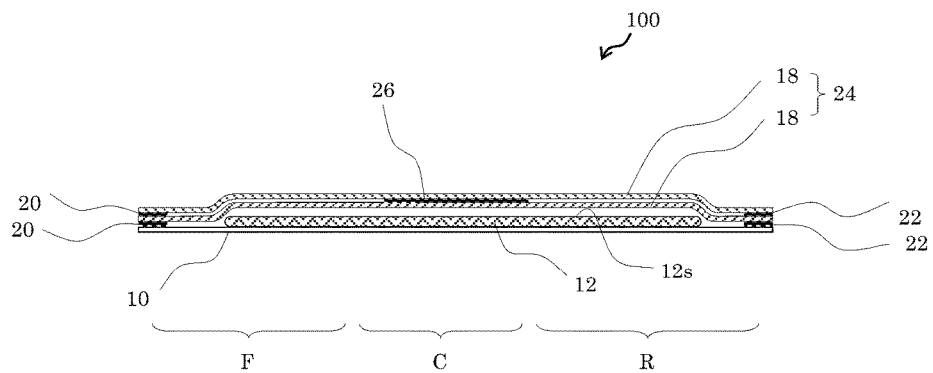

FIG. 2 contains schematic diagrams illustrating an example of an absorbent article according to the present invention. FIG. 2(A) is a developed plan view and FIG. 2 (B) is a longitudinal end view along line IIB-IIB in FIG. 2(A). FIG. 2 schematically shows the state in which stress is applied to the absorbent article such that it is pulled in the front-rear direction and the lateral direction to be developed into a substantially planar form.

Absorbent article 100 according to the present invention shown in FIG. 2 is basically provided with: leak preventer 10 in sheet form; absorber 12 capable of absorbing a bodily fluid, wherein at least one layer thereof is arranged above leak preventer 10; and a pair of right and left FLGs 14 arranged, above absorber 12, from a front end part of the absorbent article body to a rear end part thereof in a longitudinal direction, via front body F, crotch part C and rear body R.

Materials that are generally used as a back sheet can be used for the materials of leak preventer 10. In particular, a resin film made of, for example, PE, PP, PET, EVA or the like and a bodily fluid impermeable sheet such as a foam sheet made of the resin described above can be used. For the bodily fluid impermeable sheet, a sheet having air permeability, such as an air permeable sheet or the like may be preferably used.

In addition, when the above-described resin film is used, a multilayered sheet of such film and a non-woven fabric may be used in order to improve the texture and appearance. In this case, a spunbond (SB) or thermalbond non-woven fabric having a relatively low basis weight (for example, an air-through type) or the like may preferably be used as the non-woven fabric.

Moreover, a multilayered sheet of such resin film and an absorber in sheet form, which is described below, may also be used.

Further, a high water-resistant non-woven fabric may also be used. Examples of such high water-resistant non-woven fabric include an SMS non-woven fabric having a degree of water resistance of 100 mm H2O or more and an SMS non-woven fabric in which pores in a non-woven web are filled with microfibrillated cellulose (MFC) or wax so as to provide such fabric with water resistance. In this case, a high water-resistant non-woven fabric may be used alone or may also be used as a multilayered sheet of the film and such high water-resistant non-woven fabric.

Leak preventer 10 may be configured from a plurality of members.

Leak preventer 10 is in sheet form; however, it is not particularly limited in terms of shape as long as it envelopes absorber 12, or the like, above itself and is capable of being arranged with FLGs 14 thereon.

Absorber 12 used in the present invention is not particularly limited, as long as it is capable of absorbing bodily fluid, and any absorber used in publicly known conventional absorbent articles may be used. Examples such as: pulverized wood pulp; an absorber in which pulverized wood pulp and granular or powdery SAP are mixed and shaped into a mat; a sheet-like absorber formed into a thin sheet and having SAP as a primary component, or the like, may be used. These absorbers keep the shape thereof and at the same time prevent the generation and droppage of fine powder from pulp and SAP. Thus, in general, the absorbers are covered with a core wrapping material made of tissue paper, a non-woven fabric, a perforated film, or the like. In the present specification, when a core wrapping material is used, such core wrapping material is also inclusively referred to as an "absorber."

An absorber in sheet form excels in morphological stability and capability of SAP droppage prevention, etc.

Among various types of absorber in sheet form, a super absorbent sheet containing 50 weight % or more, preferably 60 weight % or more, or more preferably 70 weight % or more of SAP is preferred. In addition, from the perspective of stability, etc. of the super absorbent sheet, the content of SAP therein is preferably 95 weight % or less.

The super absorbent sheet is an extremely-thin absorber in sheet form having SAP as a primary component. Since the content of SAP is extremely high, the thickness of the super absorbent sheet is extremely low. The thickness of the super absorbent sheet is preferably 1.5 mm or less and more preferably 1 mm or less.

The super absorbent sheet is not particularly limited in terms of its configuration and production method, as long as it is an extremely-thin absorber in sheet form having SAP as a primary component.

For example, there is a super absorbent sheet obtained by an Air-Laid process. In the Air-Laid process, pulverized wood pulp and SAP are mixed and a binder is added to shape the mixture into a sheet form and then a super absorbent sheet is obtained. As examples of a super absorbent sheet obtained through this process, NOVATHIN (US registered trademark) manufactured by Rayonier Inc. in the US, B-SAP manufactured by Oji Kinocloth Co., Ltd., or the like, are known.

Another example of the super absorbent sheet includes a super absorbent sheet obtained through a process involving coating a bodily fluid permeable sheet such as a non-woven fabric with SAP-dispersed slurry. Here, the SAP-dispersed slurry is preferably prepared by dispersing SAP and microfibrillated cellulose (MFC) in a mixed solvent of water and ethanol. As an example of the super absorbent sheet obtained through this process, MegaThin (registered trademark) manufactured by Japan Absorbent Technology Institute is known.

Other examples of the super absorbent sheet include: a super absorbent sheet obtained through a process involving having a raised non-woven fabric carry a large amount of SAP and fixing the SAP with a hot melt binder, an emulsion binder, an water soluble, or the like; a super absorbent sheet obtained through a process involving mixing fibrous SAP with a PET (polyethylene terephthalate) fiber and forming the mixture into a web; and an SAP sheet obtained by providing tissues above and below an SAP layer.

At least one layer of absorber 12 is arranged above leak preventer 10. Namely, absorber 12 may be comprised of one layer or two or more layers (multilayer).

In addition, absorber 12 may be arranged in a folded condition.

A pair of right and left FLGs 14 are arranged, above absorber 12, from a front end part of the absorbent article body to a rear end part thereof in a longitudinal direction, via front body F, crotch part C and rear body R. The FLGs may be provided by being coupled to the leak preventer, may be provided by being coupled to the top sheet or the other members provided above the leak preventer, or may be provided by being coupled to a plurality of members.

FLG 14 includes head part 16 which is configured by having a stretchable member (for example, the two parallel polyurethane filaments depicted in wavy lines in FIG. 2) and hanging part 18 which continues to head part 16. FLG 14 is configured such that a front end part and a rear end part (i.e. parts where the polyurethane filaments are not present in FIG. 2) of head part 16 are respectively coupled to the vicinity of a front end part and the vicinity of a rear end part of the absorbent article body (front end coupling part 20 and rear end coupling part 22 are shown in FIG. 2) and such that hanging part 18 hangs down from head part 16 toward absorber 12. The coupling method is not particularly limited and, for example, the coupling method may be achieved by means of an adhesive.

Hanging part 18 hangs down from head part 16 in curtain form and it does not stand up due to being coupled to, fixed to and supported by the absorber (or the top sheet covering the absorber) as in conventional ILGs. Hanging part 18 is basically not fixed to surface 12$s$ of absorber 12 (however, as will be described later, a part thereof is fixed thereto) and floats from surface 12$s$ of absorber 12. Since such new FLG 14 has a floating configuration as described above, it will be herein referred to as a floating leg gather (FLG). Such floating configuration may be realized by making, for example, the length between front end coupling part 20 and rear end coupling part 22 in FLG 14 shorter than the length between the front end coupling part 20 and rear end coupling part 22 in leak preventer 10.

Parts of hanging parts 18 of the pair of right and left FLGs 14 are connected to each other in the vicinity of the lower end parts thereof.

In particular, for each of the pair of right and left FLGs 14, head part 16 is arranged to face outward and hanging part 18 is arranged to face inward. Hanging parts 18 of the pair of right and left FLGs 14 are connected to each other by overlapping with each other in the vicinity of the lower end parts thereof so as to be directly coupled to each other at connection part 26 in overlapping part 24.

In the present invention, it is sufficient when at least parts of the hanging parts are connected to each other in the vicinity of the lower end parts thereof. In other words, the entire hanging parts may be connected to each other in the vicinity of the lower end parts thereof in the front-rear direction, or parts of the hanging parts may be connected to each other in the vicinity of the lower end parts thereof in the front-rear direction.

FLG 14 is not fixed to surface 12$s$ of absorber 12 from the front end part to the rear end part and is spaced apart from surface 12$s$ of absorber 12. Namely, FLG 14 is present in a completely floating state.

In absorbent article 100, since FLGs 14 employ the above-described configuration, transferring passage P for bodily fluids is formed on the inner surface sides of hanging parts 18 at crotch part C. Transferring passage P for bodily fluids is formed by the pair of right and left hanging parts 18$b$ being coupled to each other so that the inner surfaces thereof configure both side surfaces and a bottom surface. At the time of wearing, crotch part C assumes a form such as that shown in FIG. 1(C). Since the pair of right and left head parts 16 are spaced apart, the upper part of transferring passage P for bodily fluids is open.

In front body F and rear body R, the pair of right and left FLGs 14 are not coupled to each other, and thus, at the time of wearing, each of front body F and rear body R assumes a form such as that shown in FIG. 1(A).

At the time of wearing, head parts 16 of FLGs 14 make contact with the wearer's skin but keep a spaced-apart state from surface 12$s$ of absorber 12.

Figure 3:
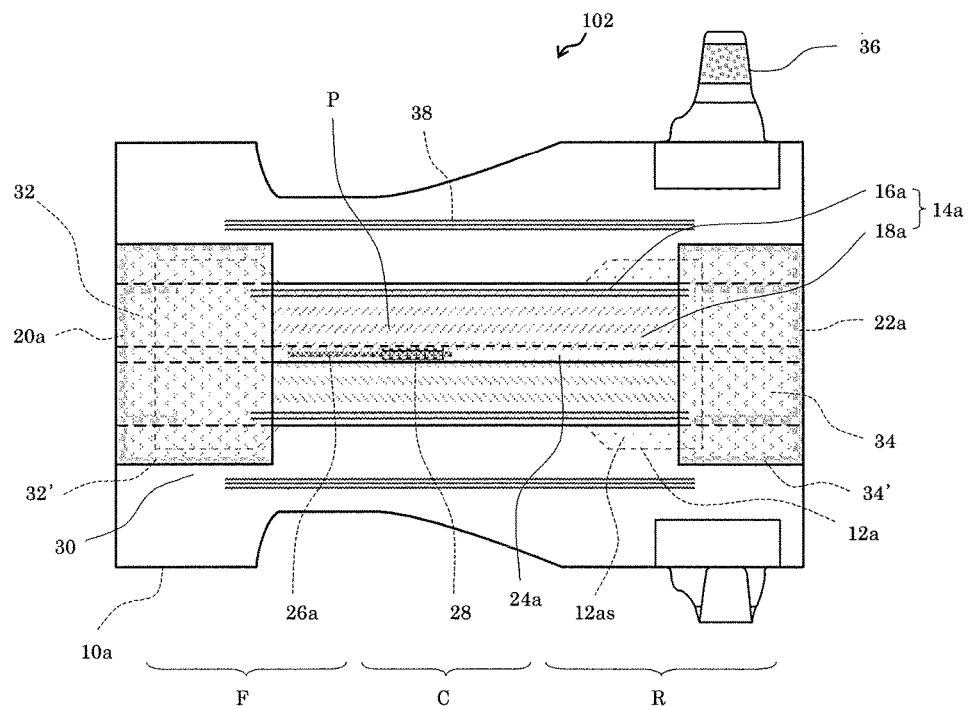
FIG. 3 is a schematic developed plan view illustrating an embodiment of the absorbent article according to the present invention.

FIG. 3 is a schematic developed plan view illustrating an embodiment of the absorbent article according to the present invention. FIG. 3 schematically shows the state in which a stress is applied to the absorbent article such that it is pulled in the front-rear direction and the lateral direction to be developed into a substantially planar form. In the description below, the size of the absorbent article and the various members and the weight of the absorbent article and the absorber are all numerical values intended for a medium-sized diaper for infants (approximately 6 kg or more in body weight); however, the present invention is not limited thereto.

Absorbent article 102 according to the present invention shown in FIG. 3 is configured as a tape-type diaper. Absorbent article 102 is basically provided with: leak preventer 10a in sheet form; absorber 12a capable of absorbing a bodily fluid, wherein at least one layer thereof is arranged above leak preventer 10a; and a pair of right and left FLGs 14a arranged, above absorber 12a, from a front end part of the absorbent article body to a rear end part thereof in the longitudinal direction, via front body F, crotch part C and rear body R.

Leak preventer 10a is configured by a sheet-form leak preventer made of a composite of an air-permeable PE film and a SMS non-woven fabric made of PP.

In a plan view, absorber 12a is formed in the shape of a sandglass. The width in the lateral direction of the parts of the front body and the rear body where the width is large is approximately 120 mm, the width in the lateral direction of the part around the crotch part is approximately 90 mm, and the length in the front-rear direction is approximately 380 mm. Absorber 12a is configured by covering 25 g of pulverized pulp and 6 g of SAP with tissue paper. Absorber 12a is arranged above leak preventer 10a and is received between leak preventer 10a and top sheet 30.

Although they differ with respect to the details such as shape, etc., leak preventer 10a and absorber 12a in absorbent article 102 respectively correspond to leak preventer 10 and absorber 12 in absorbent article 100, and thus, the descriptions thereof will be omitted, except for the above description.

Top sheet 30 is configured by an air-through non-woven fabric made of PE/PP composite fibers (for example, such fabric has a basis weight of 15 g/m2 and is manufactured by Rengo Co., Ltd.).

The size of absorbent article 102 approximately matches with that of leak preventer 10a, and the length thereof in the front-rear direction is approximately 440 mm and the width thereof in the lateral direction is approximately 270 mm. The weight of absorbent article 102 is approximately 34 g.

FLG 14a includes head part 16a and hanging part 18a that connects to head part 16a. FLG 14a is configured such that a front end part and a rear end part of hanging part 18a are respectively coupled to the vicinity of a front end part and the vicinity of a rear end part of the absorbent article body (front end coupling part 20a and rear end coupling part 22a are shown in FIG. 3) and such that hanging part 18a hangs down from head part 16a toward absorber 12a.

Head part 16a of FLG 14a is configured by covering two parallel polyurethane filaments with an SMS non-woven fabric made of PP (for example, such fabric has a basis weight of 15 g/m2 and is manufactured by AVGOL). The hanging part of such SMS non-woven fabric configures hanging part 18a. The width of head part 16a is approximately 10 mm and the width of hanging part 18a is approximately 40 mm.

Parts of hanging parts 18a of the pair of right and left FLGs 14a are connected to each other in the vicinity of the lower end parts thereof.

More particularly, for each of the pair of right and left FLGs 14a, head part 16a is arranged to face outward and hanging part 18a is arranged to face inward. Hanging parts 18a of the pair of right and left FLGs 14a are connected to each other by being overlapped with each other in the vicinity of the lower end parts thereof so as to be directly coupled to each other at connection part 26a in overlapping part 24a. The width of overlapping part 24a is approximately 10 mm. Connection part 26a extends from front body F to crotch part C and the length thereof in the front-rear direction is approximately 120 mm.

In rear body R, hanging part 18a of FLG 14a is not fixed to surface 12as of absorber 12a and is spaced apart from surface 12as of absorber 12a (i.e. a floating state). The lower end part of hanging part 18a, in particular, an under surface of overlapping part 24a of hanging part 18a is fixed to surface 12as of absorber 12a at coupling part 28 in crotch part C (corresponding to the vicinity of the rear part of connection part 26a). The length of coupling part 28 in the front-rear direction is approximately 40 mm.

Coupling part 28 is linearly provided such that it extends in the front-rear direction at the center in the lateral direction of crotch part C; however, the present invention is not limited thereto. For example, the coupling part may be configured by providing a plurality of lines (for example, a pair of right and left lines) in the lateral direction, or it may be configured by providing two or more spots or lines in the front-rear direction, and these may be used in combination as needed.

In absorbent article 102, since FLGs 14a employ the above-described configuration, transferring passage P for bodily fluids is formed on the inner surface sides of hanging parts 18a at crotch part C. Transferring passage P for bodily fluids is formed by the pair of right and left hanging parts 18a being coupled to each other so that the inner surfaces thereof configure both side surfaces and a bottom surface. At the time of wearing, a part of crotch part C where coupling part 28 is present assumes a form such as that shown in FIG. 1(D). Since the pair of right and left head parts 16a are spaced apart, the upper part of transferring passage P for bodily fluids is open.

Although the pair of right and left FLGs 14a are coupled to each other at connection part 26a in front body F, they are not coupled to surface 12as of absorber 12a. Thus, at the time of wearing, a part (approximately 80 mm) of front body F where connection part 26a is present assumes a form such as that shown in FIG. 1(C).

In addition, since the pair of right and left FLGs 14a are not coupled to each other in a part of front body F and crotch part C where connection part 26a is not present and in rear body R, at the time of wearing, a part (approximately 70 mm) forward of the part of front body F where connection part 26a is present and a part (approximately 200 mm) extending from crotch part C to rear body R where connection part 26a is not present assume a foam such as that shown in FIG. 1(A).

Namely, in absorbent article 102, all three of the above-described form types of the state of existence of the FLGs (i.e. the respective forms shown in FIGS. 1(A), 1(C) and 1(D)) are used.

Regarding transferring passage P for bodily fluids in absorbent article 102, hanging part 18a, which is a member that configures such passage, couples to surface 12as of absorber 12a in the vicinity of the rear end of transferring passage P for bodily fluids and is spaced apart from surface 12as of absorber 12a in the parts other than the rear end. Due to this, the height of transferring passage P for bodily fluids is low at the fixed part and is high at the non-fixed part.

In other words, a part of the bottom surface of transferring passage P for bodily fluids, in which hanging part 18a is present in the floating state and which has a relatively high position in the vertical direction, is present in front body F. A part of the bottom surface of transferring passage P for bodily fluids, in which hanging part 18a couples to surface 12as of absorber 12a and which has a relatively low position in the vertical direction, is present in crotch part C. Accordingly, an inclined state that lowers down from front body F toward crotch part C is achieved.

At the time of wearing, head parts 16a of FLGs 14a make contact with the wearer's skin but keep a spaced-apart state from surface 12as of absorber 12a.

In the front part and rear part of the absorbent article body, front part pocket 32 and rear part pocket 34 are respectively provided.

Front part pocket 32 is configured by an SMS non-woven fabric. As shown in FIG. 3, front part pocket 32 is formed by, after covering the entire width (approximately 90 mm) of FLGs 14a in the lateral direction in front body F with the SMS non-woven fabric (the width thereof is approximately 130 mm) from above, respectively coupling the front end part of the SMS non-woven fabric to the front end parts of the absorbent article body and FLGs 14a and the right and left edge parts of the SMS non-woven fabric (the length of the SMS non-woven fabric in the front-rear direction is approximately 100 mm) to top sheet 30 in the vicinity of the right and left edge parts of absorber 12a. Coupling part 32' is coupled using, for example, a hot-melt adhesive, and a seal for preventing bodily fluid (mainly urine) leakage is achieved along a total of three sides of the SMS non-woven fabric including the front end part and the right and left edge parts. In addition, coupling part 32' has two linear parts extending in the front-rear direction on a slightly inner side of the right and left edge parts of the SMS non-woven fabric. This enables to make the configuration of front part pocket 32 robust.

Rear part pocket 34 is configured by an SMS non-woven fabric. As shown in FIG. 3, rear part pocket 34 is formed by, after covering the entire width (approximately 90 mm) of FLGs 14a in the lateral direction in rear body R with the SMS non-woven fabric (the width thereof is approximately 130 mm) from above, respectively coupling the rear end part of the SMS non-woven fabric to the rear end parts of the absorbent article body and FLGs 14a and the right and left edge parts of the SMS non-woven fabric (the length of the SMS non-woven fabric in the front-rear direction is approximately 80 mm) to top sheet 30 in the vicinity of the right and left edge parts of absorber 12a. Coupling part 34' is coupled using, for example, a hot-melt adhesive, and a seal for preventing bodily fluid (mainly urine) leakage is achieved along a total of three sides of the SMS non-woven fabric including the rear end part and the right and left edge parts. In addition, coupling part 34' has two linear parts extending in the front-rear direction on a slightly inner side of the right and left edge parts of the SMS non-woven fabric. This enables to make the configuration of rear part pocket 34 robust.

As described above, front part pocket 32 and rear part pocket 34 have substantially the same configuration and also have the same width in the lateral direction; however, in view of the fact that urine is more likely to leak from the front, the length in the front-rear direction (i.e. the depth of the pocket) of front part pocket 32 is made longer (deeper) than that of rear part pocket 34.

When this diaper is worn, the excreted urine is received through an opening between head parts 16a of the pair of right and left FLGs 14a and is first enveloped in transferring passage P for bodily fluids which is present from crotch part C to front body F.

Since it is surrounded by hanging parts 18a of FLGs 14a, the total volume of the urine enveloped in transferring passage P for bodily fluids transfers either to the front or to the rear via transferring passage P for bodily fluids. In this example of a diaper, since transferring passage P for bodily fluids is downwardly inclined from front body F toward crotch part C, the urine tends to transfer relatively toward the rear side. It goes without saying that this also depends on the body position of the wearer. Namely, most of the enveloped urine transfers to the rear side and the remainder transfers to the front side.

The urine, which has transferred from the originally enveloped position in transferring passage P for bodily fluids to the rear side, makes a smooth transfer onto absorber 12a from the rear end part of transferring passage P for bodily fluids by transferring passage P for bodily fluids acting as a gutter. Thereafter, the urine spreads from front to back and from side to side, to be absorbed by absorber 12a. Part of the urine may reach the vicinity of the rear end part of the diaper body; however, since it is trapped by rear part pocket 34, leakage from the rear end part is suppressed.

On the other hand, most of the urine which has transferred from the originally enveloped position in transferring passage P for bodily fluids to the front side, drops from the front end part of transferring passage P for bodily fluids to be transferred into front part pocket 32 and part thereof spreads from front to back and from side to side, to be absorbed by absorber 12a.

In this way, in the absorbent article according to the present invention, an absorption mechanism is achieved in which the excreted bodily fluid (urine) is first received by transferring passage P for bodily fluids and then the received urine is transferred to the absorber. In particular, basically all of the excreted bodily fluid is supplied to the absorber via this transferring passage for bodily fluids.

Accordingly, it is extremely unlikely that side leakage will occur, which occurs when a large amount of urine is excreted and bursts onto the surface of the absorber and transfers thereover to reach the right and left edge parts of the absorbent article body, and which has been a problem in conventional absorbent articles.

In addition, the usage efficiency of the entire absorber, especially of the rear part thereof can be increased.

Moreover, in this diaper, since the transferring passage for bodily fluids basically has no or very limited function of absorbing the bodily fluids, and since the transferring passage for bodily fluids is downwardly inclined from the front body toward the crotch part, the urine does not stay within the transferring passage for bodily fluids.

In addition, since the total volume of the excreted urine is supplied onto the surface of the absorber via the transferring passage for bodily fluids, only a small portion of the excreted urine, which is attached to and remains on the bottom surface of the transferring passage for bodily fluids, is likely to make contact with the wearer's skin. Further, the head parts of the FLGs and the hanging parts which configure the side surfaces of the transferring passage for bodily fluids serve as a physical obstacle to the wearer's skin making contact with the bottom surface of the transferring passage for bodily fluids.

Accordingly, the possibility of the wearer's skin making contact with the urine is significantly reduced over the entire duration of use (i.e. life time) of the diaper from the beginning to the end of use. As a result, the wearer's skin is unlikely to become wet and also hot and stuffy state and rashes are unlikely to occur.

Next, the case of when feces are excreted will be described.

Since feces are excreted into the part, in rear body R, where the hanging parts of the FLGs are not connected to each other and where the FLGs are present in the form of the floating state (see FIG. 1(A)), the feces are received through an opening between head parts 16a of the pair of right and left FLGs 14a and guided by hanging parts 18a onto surface 12as of absorber 12a to be enveloped on surface 12as of absorber 12a.

When the feces are solid, they stay as is at the position (in many cases, in the vicinity of the center in the lateral direction) where they are enveloped. However, when the feces are watery, they spread over absorber 12a and the water content is absorbed by absorber 12a and the solid content remains on surface 12as of absorber 12a.

Contact between the excreted feces and the wearer's skin is significantly suppressed as compared to the conventional diaper, since the head parts and the hanging parts of the FLGs serve as a physical obstacle to the wearer's skin making contact with the surface of the absorber. In particular, when the feces are solid, only the periphery of the anus becomes dirty and thus, the burden of the care-taker of performing a cleaning can be reduced when this diaper is used for, for example, the elderly.

The present invention is not limited to the above-described configuration and, for example, various publicly-known conventional members may be provided.

In addition to the members described above, absorbent article 102 is provided with various other members described below.

Detachable members 36 are provided on both the right and left sides of leak preventer 10a in the vicinity of the rear end thereof. On the under surface of leak preventer 10a in the vicinity of the front end thereof, detachable members (not shown) are provided such that they can be detached from detachable members 36. These detachable members may be configured by, for example, various hook-and-loop fasteners. In particular, as for detachable members 36 provided on both the right and left sides of first leak preventer 10a in the vicinity of the rear end thereof, Velcro tapes (male) may be used. As for the detachable members provided on the under surface of leak preventer 10a in the vicinity of the front end, TLZs (female) may be used.

In addition, absorbent article 102 is provided with two types of leg gathers. In particular, in addition to the above-described FLGs 14a, OLGs 38 are provided, which are present in the side edge parts of the absorbent article body. OLG 38 is formed by three parallel polyurethane filaments (stretchable members) being arranged between leak preventer 10a and top sheet 30.

Figure 4:
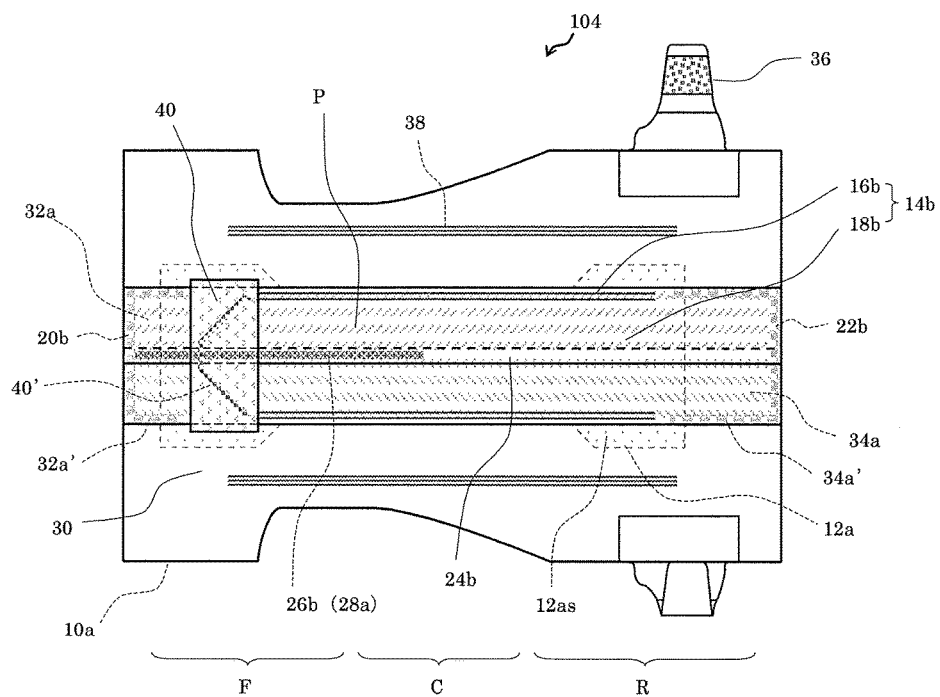
FIG. 4 is a schematic developed plan view illustrating another embodiment of the absorbent article according to the present invention.

FIG. 4 is a schematic developed plan view illustrating another embodiment of the absorbent article according to the present invention. FIG. 4 schematically shows the state in which stress is applied to the absorbent article such that it is pulled in the front-rear direction and the lateral direction to be developed into a substantially planar form. In the description below, the size of the absorbent article and the various members and the weight of the absorbent article and the absorber are all numerical values intended for a medium-sized diaper for infants (approximately 6 kg or more in body weight); however, the present invention is not limited thereto.

Absorbent article 104 according to the present invention shown in FIG. 4 is basically similar to absorbent article 102 according to the present invention shown in FIG. 3; however, it differs therefrom with respect to the point of the state of existence of the FLGs (and thus, the configuration transferring passage P for bodily fluids in accordance with such state) and of the state of existence of the various pockets.

FLG 14b includes head part 16b and hanging part 18b that connects to head part 16b and parts of the pair of right and left hanging parts 18b are connected to each other in the vicinity of the lower end parts thereof.

More particularly, for each of the pair of right and left FLGs 14b, head part 16b is arranged to face outward and hanging part 18b is arranged to face inward. Hanging parts 18b of the pair of right and left FLGs 14b are connected to each other by being overlapped with each other in the vicinity of the lower end parts thereof so as to be directly coupled to each other at connection part 26b in overlapping part 24b. The width of overlapping part 24b is approximately 10 mm. Connection part 26b extends from the front end part of the absorbent article body toward crotch part C via front body F and the length thereof in the front-rear direction is approximately 200 mm.

In rear body R, hanging part 18b of FLG 14b is not fixed to surface 12as of absorber 12a and is spaced apart from surface 12as of absorber 12a (i.e. a floating state). The lower end part of hanging part 18b, in particular, an under surface of overlapping part 26b of hanging part 18b is fixed to surface 12as of absorber 12a at coupling part 28a in crotch part C (specifically, in the part of crotch part C corresponding to connection part 26a). The length of coupling part 28a in the front-rear direction is approximately 200 mm.

In absorbent article 104, since FLGs 14b employ the above-described configuration, transferring passage P for bodily fluids is formed on the inner surface sides of hanging parts 18b from the front end part to crotch part C via front body F. Transferring passage P for bodily fluids is formed by the pair of right and left hanging parts 18b being coupled to each other so that the inner surfaces thereof configure both side surfaces and a bottom surface. At the time of wearing, a part where coupling part 28a is present from the front end part to crotch part C via front body F assumes a form such as that shown in FIG. 1(D). Since the pair of right and left head parts 16b are spaced apart, the upper part of transferring passage P for bodily fluids is open.

The pair of right and left FLGs 14b are not coupled to each other in the part of crotch part C where coupling part 28a is not present and in rear body R, and thus, at the time of wearing, a form such as that shown in FIG. 1(A) is obtained.

Namely, in absorbent article 104, two out of the three above-described form types of the state of existence of the FLGs (i.e. the respective forms shown in FIG. 1(A) and FIG. 1(D)) are used.

Transferring passage P for bodily fluids in absorbent article 104 extends up to the front end part of the absorbent article body. More specifically, the front ends of FLGs 14b couple to the absorbent article body at front end coupling parts 20b (the width thereof is approximately 90 mm). In addition, in the vicinity of the front end of transferring passage P for bodily fluids, head parts 16b of the pair of right and left FLGs 14b couple to the absorbent article body at coupling parts 32a' (the length thereof in the front-rear direction is approximately 40 mm).

Each of front end coupling parts 20b and coupling parts 32a' is coupled using, for example, a hot-melt adhesive, and a seal for preventing bodily fluid (mainly urine) leakage is achieved along a total of three sides including the front end part and the right and left edge parts of FLGs 14b.

In this way, the pair of right and left FLGs 14b form front part pocket 32a at front ends thereof In addition, passage pocket 40 is provided above the part of transferring passage P for bodily fluids at the front end thereof, which is next to front part pocket 32a. Passage pocket 40 is configured by a water-resistant sheet (the length thereof in the front-rear direction is approximately 40 mm) having a width substantially the same as the spacing between head parts 16b of the pair of right and left FLGs 14b. As shown in FIG. 4, passage pocket 40 is formed by, after covering the entire width of FLGs 14b in the lateral direction, from above, in the part in front body F which is next to front part pocket 32a with the water-resistant sheet, coupling such water-resistant sheet to hanging parts 18b of FLGs 14b at coupling parts 40'. In other words, the front end and the right and left edge parts of the part in transferring passage P for bodily fluids, which is next to front part pocket 32a, are sealed.

The rear ends of FLGs 14b couple to the absorbent article body at rear end coupling part 22b (the width thereof is approximately 90 mm). In addition, head parts 16b of the pair of right and left FLGs 14b couple to the absorbent article body at coupling parts 34a' (the length thereof in the front-rear direction is approximately 70 mm).

Each of rear end coupling part 22b and coupling parts 34a' is coupled using, for example, a hot-melt adhesive, and a seal for preventing bodily fluid (mainly urine) leakage is achieved along a total of three sides including the front end part and the right and left edge parts of FLGs 14b.

In this way, the pair of right and left FLGs 14b form rear part pocket 34a at rear ends thereof As described above, rear part pocket 32a and rear part pocket 34a have substantially the same configuration and also have the same width in the lateral direction; however, the length in the front-rear direction (i.e. the depth of the pocket) of rear part pocket 34a is made longer (deeper) than that of front part pocket 32a.

When this diaper is worn, the excreted urine is received through an opening between head parts 16b of the pair of right and left FLGs 14b and is first enveloped in transferring passage P for bodily fluids which is present from crotch part C to front body F.

Since it is surrounded by hanging parts 18b of FLGs 14b, the total volume of urine enveloped in transferring passage P for bodily fluids transfers either to the front or to the rear via transferring passage P for bodily fluids. In this example of a diaper, since hanging parts 18b, which are members configuring transferring passage P for bodily fluids, couple to surface 12as of absorber 12 from the front end of transferring passage P for bodily fluids to the rear end thereof, no inclination is present in the front-rear direction. For this reason, the urine tends to transfer to the front side as compared to absorbent article 102.

The urine transferred forward in transferring passage P for bodily fluids may temporarily stay within passage pocket 40 due to being blocked by passage pocket 40; however, the urine eventually transfers to the rear side and makes a smooth transfer onto absorber 12a from the rear end part of crotch part C, which is the only exit of transferring passage P for bodily fluids, by transferring passage P for bodily fluids acting as a gutter. Thereafter, the urine spreads from front to back and from side to side to be absorbed by absorber 12a. Part of the urine may reach the vicinity of the rear end part of the diaper body; however, since it is trapped by rear part pocket 34, leakage from the rear end part is suppressed.

It should be noted that front part pocket 32a provides a function of receiving urine in the case of, by some chance, the excreted urine overflowing from the front end part of absorber 12a.

In this way, in the absorbent article according to the present invention, an absorption mechanism is achieved in which the excreted urine is first received by the transferring passage for bodily fluids and then the received urine is transferred to the absorber.

Accordingly, it is extremely unlikely that the side leakage will occur, which occurs when a large amount of urine is excreted and bursts onto the surface of the absorber and transfers thereover to reach the right and left edge parts of the absorbent article body, and which has been a problem in conventional absorbent articles.

In addition, the usage efficiency of the entire absorber, especially of the rear part thereof can be increased.

Moreover, in this diaper, since the transferring passage for bodily fluids basically has no or very limited function of absorbing liquids, the urine does not stay within the transferring passage for bodily fluids.

In addition, since the total volume of the excreted urine is supplied onto the surface of the absorber via the transferring passage for bodily fluids, only a small portion of the excreted urine, which is attached to and remains on the bottom surface of the transferring passage for bodily fluids, is likely to make contact with the wearer's skin. Further, the head parts of the FLGs and the hanging parts which configure the side surfaces of the transferring passage for bodily fluids serve as a physical obstacle to the wearer's skin making contact with the bottom surface of the transferring passage for bodily fluids.

Accordingly, the possibility of the wearer's skin making contact with the urine is significantly reduced over the entire duration of use (i.e. life time) of the diaper from the beginning to the end of use.

The functions of the case in which feces are excreted are similar to those of the case of absorbent article 102.

Next, a description will be provided by taking a connection sheet type FLG as an example.

FIG. 5 contains schematic diagrams illustrating the principles of forming a "transferring passage for bodily fluids" by means of connection sheet type FLGs. FIG. 5 only shows FLGs, a connection sheet and an absorber of the absorbent article according to the present invention in a lateral end view.

FIG. 5(A) shows a state prior to a pair of right and left FLGs 1' being connected to each other. The pair of right and left FLGs 1' include head parts 2' and hanging parts 3' that connect to head parts 2'. A front end part and a rear end part of FLG are respectively coupled to the vicinity of a front end part and the vicinity of a rear end part of the absorbent article body (not shown), and hanging part 3' is configured to hang down from head part 2' toward absorber 4'.

As illustrated, FLGs 1' are present in a state (i.e. a floating state) in which a pair of right and left head parts 2' and hanging parts 3' hanging down from head parts 2' are floating from surface 4's of absorber 4'. This point is similar to that seen in the case of the self-connected type (see FIG. 1(A)).

In the case of a connection sheet type, hanging parts 3' of the pair of right and left FLGs 1' are connected to each other by being coupled to connection sheet 7 in the lower end parts thereof. Examples of preferred forms include: forms in which the inner surfaces of hanging parts 3' couple to connection sheet 7 (FIGS. 5(B) to 5(D)); and forms in which the outer surfaces of hanging parts 3' couple to connection sheet 8 (FIGS. 5(E) to 5(G)). Hereinafter, the respective forms will be described.

FIG. 5(B) shows a state in which, in order to enable the pair of right and left FLGs 1' to be connected to each other, each of a pair of right and left hanging parts 3' overlaps with connection sheet 7 in the vicinity of the lower end part thereof. In particular, the inner surfaces of hanging parts 3' overlap with under surfaces of the right and left edge parts of connection sheet 7. Since connection sheet 7 couples to the inner surfaces of hanging parts 3', it may hereinafter be referred to as an "inner connection sheet."

FIG. 5(C) shows a state in which the pair of right and left hanging parts 3' are connected to each other by being coupled to the under surfaces of the right and left edge parts of connection sheet 7 at connection parts 5' of the inner surfaces in the vicinity of the lower end parts thereof. In this way, transferring passage P for bodily fluids is formed on the inner surface sides of hanging parts 3'. Since the pair of right and left head parts 2' are spaced apart, the upper part of transferring passage P for bodily fluids is open.

The coupling between the pair of right and left hanging parts 3' and connection sheet 7 is sufficient when it is made at at least part of the FLGs extending in the front-rear direction. Transferring passage P for bodily fluids is formed at this coupled part. The method of coupling the pair of right and left hanging parts 3' to connection sheet 7 is not particularly limited, and the coupling may be made using, for example, a hot melt adhesive, a heated seal adhesive, or the like.

FIG. 5(D) shows a state in which a member configuring transferring passage P for bodily fluids couples to surface 4's of absorber 4' at coupling part 6'. In this form, out of the members configuring transferring passage P for bodily fluids, connection sheet 7 couples surface 4's of absorber 4'; however, the present invention is not limited thereto. The hanging parts of the FLGs may couple to the surface of the absorber or both the connection sheet and the hanging parts of the FLGs may couple to the surface of the absorber. The method of coupling the member configuring transferring passage P for bodily fluids to the surface of the absorber is not particularly limited, and the coupling may be made using, for example, a hot melt adhesive, a heated seal adhesive, or the like.

In this way, the member configuring the transferring passage for bodily fluids may either be coupled to the surface of the absorber or spaced apart from the surface of the absorber.

When, among the connection sheet types, an inner connection sheet is used, the state of existence of the FLGs is not particularly limited and various states of existence can be employed for the FLGs as long as at least parts of the hanging parts of the pair of right and left FLGs are coupled to each other by being coupled to the connection sheet by means of the inner surfaces thereof in the vicinity of the lower end parts thereof so as to form a transferring passage for bodily fluids on the inner surface sides of the hanging parts.

More specifically, out of (1) a form in which the hanging parts of the FLGs are not connected to each other and are present in a floating state (see FIG. 5(A)), (2*a*) a form in which the pair of right and left hanging parts are connected to each other by means of an inner connection sheet so as to form a transferring passage for bodily fluids and in which members configuring the transferring passage for bodily fluids are present in a floating state (see FIG. 5(C)) and (3*a*) a form in which the pair of right and left hanging parts are connected to each other by means of an inner connection sheet so as to form a transferring passage for bodily fluids and in which members configuring the transferring passage for bodily fluids are present by being coupled to the surface of the absorber (see FIG. 5(D)), it is possible to use one type or two or more types of forms including (2*a*) and/or (3*a*) in combination. In particular, a form in which only form (2*a*) is used, a form in which only form (3*a*) is used, a form in which forms (2*a*) and (3*a*) are used in combination, a form in which forms (2*a*) and (1) are used in combination, a form in which forms (3*a*) and (1) are used in combination, and a form in which forms (2*a*), (3*a*) and (1) are used in combination, may be provided. Of these, a form in which forms (2*a*) and (1) are used in combination, a form in which forms (3*a*) and (1) are used in combination and a form in which forms (2*a*), (3*a*) and (1) are used in combination are preferable.

At which position in the front-rear direction this state of existence of the FLGs is provided and how the combination is made when two or more types of forms are to be combined are the key points in designing the absorbent article.

FIG. 5(E) shows a state in which, in order to enable the pair of right and left FLGs 1' to be connected to each other, each of a pair of right and left hanging parts 3' overlaps with connection sheet 8 in the vicinity of a lower end part thereof. In particular, the outer surfaces of hanging parts 3' overlap with upper surfaces in the vicinity of the right and left edge parts of connection sheet 8. Since connection sheet 8 couples to the outer surfaces of hanging parts 3', it may hereinafter be referred to as an "outer connection sheet."

FIG. 5(F) shows a state in which the pair of right and left hanging parts 3' are connected to each other by being coupled to the upper surfaces in the vicinity of the right and left edge parts of connection sheet 8 at connection parts 5' of the outer surfaces in the vicinity of the lower end parts thereof. In this way, transferring passage P for bodily fluids is formed on the inner surface sides of hanging parts 3'. Since the pair of right and left head parts 2' are spaced apart, the upper part of transferring passage P for bodily fluids is open.

The coupling between the pair of right and left hanging parts 3' and connection sheet 8 is sufficient when it is made at least part of the FLGs extending in the front-rear direction. Transferring passage P for bodily fluids is formed at this coupled part. The method of coupling the pair of right and left hanging parts 3' to connection sheet 8 is not particularly limited, and the coupling may be made using, for example, a hot melt adhesive, a heated seal adhesive, or the like.

FIG. 5(G) shows a state in which a member configuring transferring passage P for bodily fluids couples to surface 4's of absorber 4' by mean of coupling part 6'. In this form, out of the members configuring transferring passage P for bodily fluids, connection sheet 8 couples surface 4's of absorber 4'; however, the present invention is not limited thereto. The hanging parts of the FLGs may couple to the surface of the absorber or both the connection sheet and the hanging parts of the FLGs may couple to the surface of the absorber. The method of coupling the member configuring transferring passage P for bodily fluids to the surface of the absorber is not particularly limited, and the coupling may be made using, for example, a hot melt adhesive, a heated seal adhesive, or the like.

In this way, the member configuring the transferring passage for bodily fluids may either be coupled to the surface of the absorber or spaced apart from the surface of the absorber.

When, among the connection sheet types, an outer connection sheet is used, the state of existence of the FLGs is not particularly limited and various states of existence can be employed for the FLGs as long as at least parts of the hanging parts of the pair of right and left FLGs are coupled to each other by being coupled to the connection sheet by means of the outer surfaces thereof in the vicinity of the lower end parts thereof so as to form a transferring passage for bodily fluids on the inner surface sides of the hanging parts.

More specifically, out of (1) a form in which the hanging parts of the FLGs are not connected to each other and are present in a floating state (see FIG. 5(A)), (2b) a form in which the pair of right and left hanging parts are connected to each other by means of an outer connection sheet so as to form a transferring passage for bodily fluids and in which members configuring the transferring passage for bodily fluids are present in a floating state (see FIG. 5(F)) and (3b) a form in which the pair of right and left hanging parts are connected to each other by means of an outer connection sheet so as to form a transferring passage for bodily fluids and in which members configuring the transferring passage for bodily fluids are present by being coupled to the surface of the absorber (see FIG. 5(G)), it is possible to use one type or two or more types of forms including (2b) and/or (3b) in combination. In particular, a form in which only form (2b) is used, a form in which only form (3b) is used, a form in which forms (2b) and (3b) are used in combination, a form in which forms (2b) and (1) are used in combination, a form in which forms (3b) and (1) are used in combination and a form in which forms (2b), (3b) and (1) are used in combination, may be provided. Of these, a form in which forms (2b) and (1) are used in combination, a form in which forms (3b) and (1) are used in combination and a form in which forms (2b), (3b) and (1) are used in combination are preferable.

At which position in the front-rear direction this state of existence of FLGs is provided and how the combination is made when two or more types of forms are to be combined are the key points in designing the absorbent article.

FIG. 6 is a schematic developed plan view illustrating another example of the absorbent article according to the present invention. FIG. 6 schematically shows the state in which stress is applied to the absorbent article such that it is pulled in the front-rear direction and the lateral direction to be developed into a substantially planar form.

Absorbent article 106 shown in FIG. 6 is basically similar to absorbent article 100 shown in FIG. 2; however, the shape, the state of existence, the connection form, or the like, of the FLGs are different.

FLG 14c includes head part 16c and hanging part 18c which connects to head part 16c. FLG 14c is configured such that a front end part and a rear end part of hanging part 18c are respectively coupled to the vicinity of a front end part and the vicinity of a rear end part of the absorbent article body (front end coupling part 20c and rear end coupling part 22c are shown in FIG. 6) and such that hanging part 18c hangs down from head part 16c toward absorber 12c.

Parts of hanging parts 18c of the pair of right and left FLGs 14c are connected to each other by means of connection sheet 42 in the vicinity of the lower end parts thereof.

More particularly, for each of the pair of right and left FLGs 14c, head part 16c is arranged to face outward and hanging part 18c is arranged to face inward. Hanging parts 18c of the pair of right and left FLGs 14c are arranged with spacing d maintained therebetween, and are coupled to each other by the inner surfaces (i.e. the upper surfaces) thereof being overlapped with the under surfaces of the right and left edge parts of connection sheet 42 in the vicinity of the lower end parts thereof and by being coupled to connection sheet 42 at connection parts 44.

The pair of right and left hanging parts 18c face each other with spacing d maintained therebetween. The length of spacing d is not particularly limited; however, it is preferably approximately 20 to 80 mm in the case of, for example, an infant's diaper (medium-sized). In addition, in absorbent article 106, spacing d is constant from the front end part of the absorbent article body to the rear end part thereof; however, the present invention is not limited thereto.

The under surface of connection sheet 42 is fixed to surface 12s of absorber 12 at connection part 46 in the vicinity of the rear end part of connection sheet 42 in crotch part C.

Connection sheet 42 is not fixed to surface 12s of absorber 12 and is spaced apart from surface 12s of absorber 12 (i.e. a floating state) in parts of connection sheet 42, except for the vicinity of the rear end part thereof, in crotch part C.

In absorbent article 106, since FLGs 14c employ the above-described configuration, transferring passage P for bodily fluids is formed on the inner surface sides of hanging parts 18c from front body F to crotch part C. Transferring passage P for bodily fluids is formed by the pair of right and left hanging parts 18c being coupled to connection sheet 42 so that the inner surfaces of hanging parts 18c mainly configure both side surfaces and connection sheet 42 mainly configures a bottom surface. Thus, the part in crotch part C where coupling part 46 is present assumes a form such as that shown in FIG. 5(D) at the time of wearing. Since the pair of right and left head parts 16c are spaced apart, the upper part of transferring passage P for bodily fluids is open.

In the part from front body F to crotch part C where coupling part 46 is not present, the pair of right and left FLGs 14c are connected to each other by means of connection sheet 42; however, connection sheet 42 is not coupled to surface 12s of absorber 12, and thus, a form such as that shown in FIG. 5(C) is obtained at the time of wearing.

In the parts in front body F and rear body R where connection sheet 42 is not present, the pair of right and left FLGs 14c are not coupled to each other, and thus, a form such as that shown in FIG. 5(A) is obtained at the time of wearing.

Namely, in absorbent article 106, all three of the above-described form types of the state of existence of the FLGs (i.e. the respective forms shown in FIGS. 5(A), 5(C) and 5(D)) are used.

It should be noted that absorbent article 160 shown in FIG. 6 is of an inner connection type that makes use of an inner connection sheet from among the different types of connection sheet types. In the parts where hanging parts 18c of FLGs 14c and connection sheet 42 overlap each other, absorber 12, FLGs 14c and connection sheet 42 are arranged in this order from bottom to top. However, in contrast, when the absorber, the connection sheet and the FLGs are arranged in this order from bottom to top, an outer connection type (see FIGS. 5(F) and 5(G)) that makes use of an outer connection sheet from among the different types of connection sheet types may be obtained.

An absorbent article of a connection sheet type has a first advantage to the effect that, since the width of the bottom surface of transferring passage P for bodily fluids can be easily increased; the sectional area of passage P for bodily fluids can be increased so that a reception amount of bodily fluids can be increased.

In addition, an absorbent article of a connection sheet type has a second advantage to the effect that new capability can be added by means of the connection sheet. This second advantage will be described below.

FIGS. 7 and 8 respectively contain schematic diagrams illustrating various connection sheets. Each of FIGS. 7(A) to 7(E), FIGS. 8(A), 8(C) and 8(E) is a plan view, FIG. 8(B) is a lateral end view along line VIIIB-VIIIB in FIG. 8(A), and FIG. 8(D) is a lateral end view along line VIIID-VIIID in FIG. 8(C).

Connection sheet 42*a* shown in FIG. 7(A) is strip-shaped (tape-shaped), and length L thereof in the front-rear direction is significantly longer than width W thereof in the lateral direction. Width W is preferably 20 to 50 mm and length L is preferably 100 to 300 mm. Width W is preferably 20 to 50 mm and length L is preferably twice or more of width W and is more preferably three times or more of width W. In the rear part of connection sheet 42*a*, connection parts 44*a* are provided for coupling to the hanging parts of the pair of right and left FLGs. In the case of an inner connection type absorbent article, connection parts 44*a* are provided to the under surface of the connection sheet and in the case of an outer connection type absorbent article, connection parts 44*a* are provided to the upper surface of the connection sheet (the same applies to the other connection sheets shown in FIGS. 7 and 8).

Connection sheet 42*b* shown in FIG. 7(B) is longitudinal and has a substantially rectangular shape. Length L thereof in the front-rear direction is longer as compared to width W thereof in the lateral direction; however, the width is larger as compared to that of the strip-shaped (tape-shaped) connection sheet 42*a*. Width W is preferably 50 to 100 mm and length L is preferably 100 to 300 mm. In the rear part of connection sheet 42*b*, connection parts 44*b* are provided for coupling to the hanging parts of the pair of right and left FLGs. Connection sheet 42*b* is mainly used as an outer connection sheet; however, it may also be used as an inner connection sheet.

Connection sheet 42*c* shown in FIG. 7(C) is longitudinal and has a substantially rectangular shape. Connection sheet 42*c* has the same shape (as well as the same length L and width W) as that of connection sheet 42*b*; however, it differs therefrom with respect to the point that connection parts 44*c* and 44*c*' are provided for coupling to the hanging parts of the pair of right and left FLGs.

Connection parts 44*c* are provided in the vicinity of the right and left edge parts of the front part of connection sheet 42*c* and are provided for coupling to the upper parts (in the vicinity of the head parts) of the hanging parts of the FLGs. On the other hand, connection parts 44*c*' are provided in the vicinity of the center in the lateral direction of the rear part of connection sheet 42*c* and are provided for coupling to the lower parts (in the vicinity of the lower ends) of the hanging parts of the FLGs.

Since connection sheet 42*c* couples to the hanging parts of the FLGs with such connection parts 44*c* and 44*c*', an inclined state is achieved in which the bottom surface of transferring passage P for bodily fluids is higher in the front and lower in the rear. As seen above, one of the preferable forms of the absorbent article according to the present invention is that a height difference is provided in the front-rear direction of the transferring passage for bodily fluids due to the fact that there are a plurality of positions in the vertical direction for coupling the hanging parts of the pair of right and left FLGs to the connection sheet along the front-rear direction.

Connection sheet 42*d* shown in FIG. 7(D) is longitudinal and has a substantially rectangular shape. Width W thereof in the lateral direction is longer as compared to length L thereof in the front-rear direction. Width W is preferably 100 to 250 mm and length L is preferably 50 to 200 mm. As in this case, it is one of the preferable forms of the present invention to have the length of the connection sheet in the front-rear direction not exceed the width of the connection sheet in the lateral direction.

Connection parts 44*d* for coupling to the hanging parts of the pair of right and left FLGs are provided in the vicinity of the center in the lateral direction from the front part to the rear part of connection sheet 42*d*. Connection sheet 42*d* is mainly used as an outer connection sheet; however, it may also be used as an inner connection sheet.

Connection sheet 42*e* shown in FIG. 7(E) is longitudinal and has a substantially square shape with the front end thereof being wide and the rear end thereof being narrow. Length L thereof in the front-rear direction is longer as compared to width W1 and W2 in the lateral direction. Width W1 is preferably 50 to 100 mm and width W2 is preferably 20 to 50 mm. Length L is preferably 50 to 250 mm.

Connection parts 44*e* are provided in the vicinity of the right and left edge parts of the front part of connection sheet 42*e* and are provided for coupling to the upper parts (the vicinity of the head parts) of the hanging parts of the FLGs. On the other hand, connection parts 44*e*' are provided in the vicinity of the right and left edge parts of the rear part of connection sheet 42*e* and are provided for coupling to the lower parts (the vicinity of the lower ends) of the hanging parts of the FLGs.

Since connection sheet 42*e* couples to the hanging parts of the FLGs with such connection parts 44*e* and 44*e*', an inclined state is achieved in which the bottom surface of transferring passage P for bodily fluids is higher in the front and lower in the rear.

Connection sheet 42*e* shown in FIG. 7(E) is longitudinal and has a substantially square shape with the front end thereof being wide and the rear end thereof being narrow. However, a longitudinal connection sheet with the front and rear reversed, i.e. with the front end thereof being narrow and the rear end thereof being wide, may also be used. In this case, the bottom surface of transferring passage P for bodily fluids is lower in the front and higher in the rear, and an inclined state which is the reverse of that seen in connection sheet 42*e* can be achieved.

The capacity of transferring passage P for bodily fluids is determined mainly by the sectional area of the passage. Although this may vary depending on the shape, when transferring passage P for bodily fluids is formed by, for example, a bottom surface and both side surfaces, the sectional area of the passage depends on the width of the bottom surface in the lateral direction and the height of the side surfaces in the vertical direction.

Here, the width of the bottom surface in the lateral direction is mainly defined by the distance between the lower ends of the pair of hanging parts. The height of the side surfaces in the vertical direction is mainly defined by the length (i.e. the height in the vertical direction) of the hanging part. Thus, it would be difficult to increase capacity while retaining the shape of transferring passage P for bodily fluids.

In contrast, the present inventors have conceived of increasing the capacity by devising shapes of transferring passage P for bodily fluids as described below.

Connection sheet 42f shown in FIGS. 8(A) and 8(B) is a folded-back type connection sheet.

Connection sheet 42f has a shape in which right and left edge parts of a rectangular sheet are folded inwardly on the upper side. Width W thereof is preferably 50 to 150 mm and length L thereof is preferably 100 to 300 mm. Distance d between the edge parts of the folded-back parts is preferably 20 to 80 mm, depending on the distance between the hanging parts of the pair of right and left FLGs.

In the vicinity of the right and left edge parts of the folded-back parts of connection sheet 42f, connection parts 44f are provided for coupling to the hanging parts of the pair of right and left FLGs from the front part to the rear part.

Since connection sheet 42f has folded-back parts, the sectional area, at the time of bodily fluid excretion, of transferring passage P for bodily fluids formed with such parts is significantly larger than that of the case where no such folded-back part is provided.

Connection sheet 42g shown in FIGS. 8(C) and 8(D) is a collapsible type connection sheet.

Connection sheet 42g has a shape in which right and left edge parts of a rectangular sheet are folded back inwardly on the upper side and then the inwardly-folded-back parts are further folded back outwardly. Width W thereof is preferably 50 to 150 mm and length L thereof is preferably 100 to 300 mm. Distance d between the innermost parts of the folded-back parts is preferably 20 to 80 mm, depending on the distance between the hanging parts of the pair of right and left FLGs.

In the vicinity of the right and left edge parts of the folded-back parts of connection sheet 42g, connection parts 44g are provided for coupling to the hanging parts of the pair of right and left FLGs from the front part to the rear part.

Since connection sheet 42g has double folded-back parts (i.e. collapsible parts), the sectional area, at the time of bodily fluid excretion, of transferring passage P for bodily fluids formed with such parts is significantly larger than that of the case where no such double folded-back part is provided.

When a folded-back type or collapsible type connection sheet such as that described above is used, the sectional area of transferring passage P for bodily fluids increases at the time of bodily fluid excretion, and thus, a diaper having extra space for receiving bodily fluids can be designed.

Connection sheet 42h shown in FIG. 8(E) is a connection sheet in which strip-shaped (tape-shaped) sheet 42h' and lateral sheet 42h" having a substantially rectangular shape are combined. In particular, connection sheet 42h can be obtained by arranging and coupling sheet 42h" on/to the underside of sheet 42h'. The preferable size of sheet 42h' is similar to that of connection sheet 42a shown in FIG. 7(A) above. The preferable size of sheet 42h" is similar to that of connection sheet 42d shown in FIG. 7(D) above.

In the vicinity of the right and left edge parts of sheet 42h" from the front part to the rear part thereof, connection parts 44h are provided for coupling to the hanging parts of the pair of right and left FLGs. Connection sheet 42h is mainly used as an outer connection sheet; however, it may also be used as an inner connection sheet.

Sheet 42h' of connection sheet 42h is preferably configured by a hydrophilic material and sheet 42h" thereof is preferably configured by a hydrophobic material. In this case, since sheet 42h" that forms the right and left edge parts of the bottom surface of transferring passage P for bodily fluids or parts between the right and left edge parts of the bottom surface and the side surfaces exhibits hydrophobicity and sheet 42h' that forms the center part in the lateral direction of the bottom surface of transferring passage P for bodily fluids exhibits hydrophilicity, the bodily fluids tend to transfer from the right and left edge parts to the center part and thus, a smooth transferring of bodily fluids is possible.

As for the materials to be used for connection sheets, similar to the hanging parts of the FLGs forming the side surfaces of transferring passage P for bodily fluids, preferable examples include a hydrophobic non-woven fabric such as an SB non-woven fabric, an SMS non-woven fabric, and the like, made of PE and/or PP and having water resistance.

In addition, preferable examples further include: a composite material in which a hydrophilic non-woven fabric and a water-resistant non-woven fabric are combined (for example, in connection sheet 42h shown in FIG. 8(E), sheet 42h' is configured from a hydrophilic material and sheet 42h" is configured with a hydrophobic material); a tissue/PE resin laminate in which a water-resistant material is compounded and integrated with a hydrophilic sheet; a TCF/PE film junction material, or the like.

It is important for the connection sheet to be made of a material for receiving bodily fluids and also for transferring the same in a smooth manner, so as to form the bottom surface of transferring passage P for bodily fluids. For this purpose, the connection sheet preferably has both water resistance and bodily fluid permeability.

The connection sheet may be configured from a hydrophilic material, a hydrophobic material, a combination of a hydrophilic material and a hydrophobic material, or a material in which hydrophilicity and hydrophobicity are compounded.

In the present invention, preferable examples of a hydrophilic material include: a non-woven fabric formed by mixing hydrophilic fibers such as tissue, rayon, lyocell, cotton, PVA, or the like; and a non-woven fabric provided with water penetrability by way of surfactant treatment on a spun-melt non-woven fabric such as an SB non-woven fabric, an SMS non-woven fabric, or the like.

Preferable examples of a hydrophobic material or water-resistant material include: thin and relatively soft films such as a PE film, PP film, EVA film, elastomer film, or the like; and water-resistant spunmelt non-woven fabrics having PE, PP, PE/PP, PE/PET, or the like, as a primary component.

Examples of a combination of a hydrophilic material and a hydrophobic material include those combining, as needed, any hydrophilic material described above and any hydrophobic material described above.

Examples of a material in which hydrophilicity and hydrophobicity are compounded include: a laminated sheet of a PE film and tissue; a laminated film of an SMS non-woven fabric made of PP and tissue; and a laminated sheet of an SM non-woven fabric made of PP and a cellulose-based non-woven fabric.

Hereinafter, an absorbent article according to the present invention provided with a connection sheet-type FLG will be described more specifically, based on embodiments.

FIG. 9 contains schematic diagrams illustrating a further embodiment of the absorbent article according to the present invention. FIG. 9(A) is a planar developed view that schematically illustrates the state in which stress is applied to the absorbent article such that it is pulled in the front-rear direction and the lateral direction to be developed into a substantially planar form. FIG. 9(B) is a longitudinal sectional view along line IXB-IXB in FIG. 9(A) when stress is not applied to the absorbent article (i.e. in a relaxed state).

Absorbent article 108 shown in FIG. 9 is configured as a tape-type diaper and is basically similar to absorbent article 102 according to the present invention shown in FIG. 3.

However, it differs therefrom with respect to the point that the FLGs are connected by means of a connection sheet (and thus, the configuration of transferring passage P for bodily fluids in accordance with such point), as well as with respect to the point that a front part pocket and a rear part pocket are not provided. In the description below, the size of the absorbent article and the various members and the weight of the absorbent article and the absorber are all numerical values intended for a medium-sized diaper for infants (approximately 6 kg or more in body weight); however, the present invention is not limited thereto. The same applies to absorbent article 110 shown in FIG. 10 and absorbent article 112 shown in FIG. 11.

A pair of right and left FLGs 14d include head parts 16d and hanging parts 18d which connect to head parts 16d. FLG 14d is configured such that a front end part and a rear end part of hanging part 18d respectively couples to the vicinity of a front end part and the vicinity of a rear end part of the absorbent article body (front end coupling part 20d and rear end coupling part 22d are shown in FIG. 9) and such that hanging part 18d hangs down from head part 16d toward absorber 12a.

Parts of hanging parts 18d of the pair of right and left FLGs 14d are connected to each other by means of connection sheet 42i in the vicinity of the lower end parts thereof.

In particular, for each of the pair of right and left FLGs 14d, head part 16d is arranged to face outward and hanging part 18d is arranged to face inward. Hanging parts 18d of the pair of right and left FLGs 14d are connected to each other by the outer surfaces (i.e. under surfaces) thereof being coupled to connection sheet 42i at connection parts 44i in the vicinity of the lower end parts thereof.

The material configuring connection sheet 42i is a laminated sheet (manufactured by Oji Paper Co., Ltd.) of tissue (having a basis weight of 20 g/m2) and LLDPE (having a thickness of 20 μm).

Similar to connection sheet 42d shown in FIG. 7(D), connection sheet 42i is a lateral connection sheet having a substantially rectangular shape and width W thereof in the lateral direction is longer as compared to length L thereof in the front-rear direction. Width W is 110 mm and length L is 100 mm. In the vicinity of the center in the lateral direction of connection sheet 42i, from the front part thereof to the rear part thereof, and at the front end part of connection sheet 42i, the coupling is made with hanging parts 18d of the pair of right and left FLGs 14d at connection parts 44i. Connection sheet 42i is used as an outer connection sheet.

The edge part of the rear end of connection sheet 42i is coupled to surface 12as of absorber 12a over the entire lateral direction thereof at coupling part 46a. The width of coupling part 46a is approximately 10 mm.

FLGs 14d and connection sheet 42i having the above-described configurations may be provided by, for example, the following method.

First, the edge part of the rear end of connection sheet 42i is made to couple to surface 12as of absorber 12a at coupling part 46a, using a hot-melt adhesive.

Subsequently, FLGs 14d are arranged under tension such that head parts 16d face outward, hanging parts 18d face inward and distance d between the lower ends of hanging parts 18d is 20 mm. The front and rear end parts of FLGs 14d and the front and rear end parts of the diaper body are respectively coupled to each other at front end coupling parts 20d and rear end coupling parts 22d, by means of a hot-melt adhesive.

At the same time as above, the vicinity, and the like, of hanging parts 18d of FLGs 14d are coupled to connection sheet 42i, which is provided in advance above surface 12as of absorber 12a, at connection parts 44i that have a length of 100 mm in the front-rear direction, by means of a hot-melt adhesive. In this way, transferring passage P for bodily fluids having a length of 100 mm is formed from front body F to crotch part C.

Connection sheet 42i is fixed by the rear end part thereof being coupled to surface 12as of absorber 12a. Accordingly, the bottom surface of transferring passage P for bodily fluids formed by means of connection sheet 42i achieves an inclined state in which the height of the arrangement position lowers down from the front end part to the rear end part (see, in particular, FIG. 9(B)).

Accordingly, in absorbent article 108: the part of coupling part 46a in crotch part C assumes form (3b) in which the pair of right and left hanging parts are connected to each other by means of an outer connection sheet so as to form a transferring passage for bodily fluids and in which members configuring such transferring passage for bodily fluids are present by being coupled to the surface of the absorber (see FIG. 5(G)); the part from front body F to crotch part C, where connection sheet 42i is present (except for the part of coupling part 46a) assumes form (2b) in which the pair of right and left hanging parts are connected to each other by means of an outer connection sheet so as to form a transferring passage for bodily fluids and in which members configuring the transferring passage for bodily fluids are present in a floating state (see FIG. 5(F)); and the parts other than the above assume form (1) in which the hanging parts of the FLGs are not connected to each other and are present in a floating state (see FIG. 5(A)). Thus, three types of forms are used in combination.

FIG. 10 is a schematic developed plan view illustrating a further example of the absorbent article according to the present invention. FIG. 10 schematically shows the state in which stress is applied to the absorbent article such that it is pulled in the front-rear direction and the lateral direction to be developed into a substantially planar form.

Absorbent article 110 shown in FIG. 10 is configured as a tape-type diaper and is basically similar to absorbent article 108 according to the present invention shown in FIG. 9; however, it differs therefrom in terms of the shape and the state of arrangement of the connection sheet.

Parts of hanging parts 18d of the pair of right and left FLGs 14d are connected to each other by means of connection sheet 42j in the vicinity of the lower end parts thereof.

In particular, for each of the pair of right and left FLGs 14d, head part 16d is arranged to face outward and hanging part 18d is arranged to face inward. Hanging parts 18d of the pair of right and left FLGs 14d are connected to each other by the inner surfaces (i.e. upper surfaces) thereof being coupled to connection sheet 42j at connection parts 44j and 44j' in the vicinity of the lower end parts thereof.

Similar to the preferable form of connection sheet 42h shown in FIG. 8(E), connection sheet 42j is configured by combining hydrophilic sheet 42j' and hydrophobic sheet 42j". Specifically, connection sheet 42j has a configuration in which hydrophobic sheet 42j" consisting of an SMS non-woven fabric made of PP (having a basis weight of 15 g/m2 and manufactured by AVGOL) with a width in the lateral direction of 130 mm and a length in the front-rear direction of 180 mm, and hydrophilic sheet 42j', which is on top of hydrophobic sheet 42j"', consisting of TCF (having a basis weight of 25 g/m2 and manufactured by Futamura Chemical Co., Ltd.) with a width in the lateral direction of 50 mm and a length in the front-rear direction of 215 mm, are coupled together by means of a hot-melt adhesive, and the rear end part of sheet 42j' projects by 35 mm into the rear body direction.

The front part of sheet 42j'' of connection sheet 42j couples to the upper parts of hanging parts 18d of the pair of right and left FLGs 14d at connection parts 44j. In addition, the rear part of sheet 42j' of connection sheet 42j couples to the lower parts of hanging parts 18d of the pair of right and left FLGs 14d at connection parts 44j'. Connection sheet 42j is used as an inner connection sheet.

The center part of the rear end in the lateral direction of connection sheet 42j couples to surface 12as of absorber 12a at coupling part 46b. The length of coupling part 46b in the front-rear direction is approximately 85 mm.

As described above, the front part of connection sheet 42j couples to the upper parts of hanging parts 18d, the rear part thereof couples to the lower parts of hanging parts 18d, and the rear end part thereof couples to surface 12as of absorber 12a, and thus, connection sheet 42j is fixed. Accordingly, the bottom surface of transferring passage P for bodily fluids formed by means of connection sheet 42j achieves an inclined state in which the height of the arrangement position lowers down from the front end part to the rear end part.

Accordingly, in absorbent article 110: the part of coupling part 46b in crotch part C assumes form (3a) in which the pair of right and left hanging parts are connected to each other by means of an inner connection sheet so as to form a transferring passage for bodily fluids and in which members configuring the transferring passage for bodily fluids are present by being coupled to the surface of the absorber (see FIG. 5(D)); the part from front body F to crotch part C, where connection sheet 42j is present (except for the part of coupling part 46b) assumes form (2a) in which the pair of right and left hanging parts are connected to each other by means of an inner connection sheet so as to form a transferring passage for bodily fluids and in which members configuring the transferring passage for bodily fluids are present in a floating form (see FIG. 5(C)); and the parts other than the above assume form (1) in which the hanging parts of the FLGs are not connected to each other and are present in a floating state (see FIG. 5(A)). Thus, three types of forms are used in combination.

In absorbent article 110, connection sheet 42j is provided beyond the rear end of the parts (i.e. the parts from the front end of coupling part 44j to the rear end of coupling part 44j') of hanging parts 18d of FLGs 14d, which form transferring passage P for bodily fluids. In this way, the excreted bodily fluids can transfer smoothly from the exit in the rear part of transferring passage P for bodily fluids onto surface 12as of absorber 12a.

However, the present invention is not limited thereto, and one of the preferable forms includes the connection sheet being provided beyond the front end and/or the rear end of the parts of the hanging parts of the pair of right and left FLGs, which form a transferring passage for bodily fluids.

FIG. 11 is a schematic developed plan view illustrating a further example of the absorbent article according to the present invention. FIG. 11 schematically shows the state in which stress is applied to the absorbent article such that it is pulled in the front-rear direction and the lateral direction to be developed into a substantially planar form.

Absorbent article 112 shown in FIG. 11 is configured as a tape-type diaper and is basically similar to absorbent article 108 according to the present invention shown in FIG. 9; however, it differs therefrom in terms of the shape and the state of arrangement of the connection sheet and the provision of a passage pocket.

Parts of hanging parts 18d of the pair of right and left FLGs 14d are connected to each other by means of connection sheet 42k in the vicinity of the lower end parts thereof.

In particular, for each of the pair of right and left FLGs 14d, head part 16d is arranged to face outward and hanging part 18d is arranged to face inward. Hanging parts 18d of the pair of right and left FLGs 14d are connected to each other by the outer surfaces (i.e. under surfaces) thereof being coupled to connection sheet 42k at connection parts 44k in the vicinity of the lower end parts thereof.

Similar to connection sheet 42 shown in FIG. 7(A), connection sheet 42k is a strip-shaped (tape-shaped) connection sheet and is a hydrophobic sheet consisting of an SMS non-woven fabric made of PP (for example, having a basis weight of 15 g/m2 and manufactured by AVGOL) with a width in the lateral direction of 50 mm and a length in the front-rear direction of 190 mm.

Connection sheet 42k couples to the lower end parts of hanging parts 18d of the pair of right and left FLGs 14d at connection parts 44k over substantially the entire length in the front-rear direction. Connection sheet 42k is used as an outer connection sheet.

The center part in the lateral direction of connection sheet 42k couples to surface 12as of absorber 12a at connection part 46c over substantially the entire length in the front-rear direction. Accordingly, the bottom surface of transferring passage P for bodily fluids has substantially the same height from the front end part to the rear end part.

Passage pocket 40a is provided above the front end of transferring passage P for bodily fluids. Passage pocket 40a is configured by a water-resistant sheet (for example, an SMS non-woven fabric having a basis weight of 15 g/m2 and manufactured by AVGOL) having a width substantially the same as the spacing between headings 16d of the pair of right and left FLGs 14d. Passage pocket 40a is formed by, after covering the entire width in the lateral direction of FLGs 14d, from above, with such water-resistant sheet, coupling such water-resistant sheet to the hanging parts 18d of FLGs 14 at coupling part 40a'. As shown in FIG. 11, coupling part 40a' is provided from the front end of passage pocket 40a to the right and left edge parts thereof and the inside of passage pocket 40a is a sealed space.

Passage pocket 40a has substantially the same configuration as that of passage pocket 40 shown in FIG. 4; however, since the pair of right and left hanging parts 18d are coupled to each other via connection sheet 42k, the width in the lateral direction of transferring passage P for bodily fluids is wider. As a result, the width of passage pocket 40a is also wider and thus, the overflowing of urine is unlikely to occur. It should be noted that, in order to increase the sectional area of transferring passage P for bodily fluids, a folded-back type connection sheet (for example, connection sheet 42f shown in FIGS. 8(A) and (B)) and a collapsible type connection sheet (for example, connection sheet 42g shown in FIGS. 8(C) and (D)) may be used as the connection sheet as described above.

As described above, in absorbent article 112 shown in FIG. 11, transferring passage P for bodily fluids thereof is not inclined as in the respective transferring passages P for bodily fluids in absorbent article 108 shown in FIG. 9 and absorbent article 110 shown in FIG. 10, and thus, the excreted urine tends to transfer to the front side as well. For this reason, the front end of transferring passage P for bodily fluids is sealed by means of passage pocket 40a so as to prevent the urine from transferring forward from the front end of transferring passage P for bodily fluids.

In absorbent article 112: the part of coupling part 46c from front body F to crotch part C assumes form (3b) in which the pair of right and left hanging parts are connected to each other by means of an outer connection sheet so as to form a transferring passage for bodily fluids and in which members configuring the transferring passage for bodily fluids are present by being coupled to the surface of the absorber (see FIG. 5(G)); and the parts other than the above assume form (1) in which the hanging parts of the FLGs are not connected to each other and are present in a floating state (see FIG. 5(A)). Thus, two types of forms are used in combination.

As described above, the absorbent article according to the present invention is illustrated based on the respective embodiments illustrated herein; however, the present invention is not limited thereto and, for example, the configurations of the respective parts may be replaced with any configuration capable of performing a similar function.

In addition, the configurations of the respective parts in the respective embodiments may be combined in an arbitrary manner to obtain other embodiments.

The absorbent article according to the present invention may be preferably used for paper diapers (for infants and adults), incontinence articles, training pants, or the like.

DESCRIPTIONS OF REFERENCE NUMERALS 1, 1',14, 14a, 14b, 14c, 14d floating leg gather (FLG)
2, 2', 16, 16a, 16b, 16c, 16d head part
3, 3', 18, 18a, 18b, 18c, 18d hanging part
4, 4', 12, 12a absorber
4s, 4's, 12s, 12as surface of the absorber
5, 5', 26, 26a, 26b, 44, 44a, 44b, 44c, 44c', 44d, 44e, 44e', 44f, 44g, 44h, 44i, 44j, 44j',
44k connection part
6, 6', 28, 28a, 32', 32a', 34', 34a', 40', 40a', 46, 46a, 46b, 46c coupling part
7, 8, 42, 42a, 42b, 42c, 42d, 42e, 42f, 42g, 42h, 42i, 42j, 42k connection sheet
10, 10a leak preventer
20, 20a, 20b, 20c, 20d front end coupling part
22, 22a, 22b, 22c, 22d rear end coupling part
24, 24a, 24b overlapping part
30 top sheet
32, 32a front part pocket
34, 34a rear part pocket
36 detachable member
38 outer leg gather (OLG)
40, 40a passage pocket
42h', 42h'', 42j', 42j'' sheet
100, 102, 104, 106, 108, 110, 112 absorbent article
C crotch part
F front body
P transferring passage for bodily fluids
R rear body

The invention claimed is:
1. An absorbent article including:
a leak preventer in sheet form;
an absorber capable of absorbing a bodily fluid, wherein at least one layer thereof is arranged above the leak preventer; and
a pair of right and left floating leg gathers, in which the right floating leg gather is disposed on a right side of the absorbent article and the left floating leg gather is disposed on a left side of the absorbent article, the pair of right and left floating leg gathers are arranged, above the absorber, from a front end part to a rear end part in a length direction of a body of the absorbent article via a front body, a crotch part and a rear body;
wherein the floating leg gather has a head part and a hanging part that connects to the head part,
wherein a front end part and a rear end part of the floating leg gather respectively couple to the vicinity of the front end part and the rear end part of the body of the absorbent article, the hanging part being configured to hang down from the head part toward the absorber,
wherein the hanging part is not connected to a surface of the absorber or the hanging part has a part that is not connected to a surface of the absorber and a part that is connected to the surface of the absorber,
wherein at least parts of the hanging parts of the pair of right and left floating leg gathers are connected to each other above the absorber in the vicinity of lower end parts thereof such that an inner surface side of each of the hanging parts face each other to form a transferring passage for bodily fluids, and
wherein the hanging part is liquid-impermeable.

2. The absorbent article according to claim 1, wherein an upper part of the transferring passage for bodily fluids is open.

3. The absorbent article according to claim 1, wherein for each of the pair of right and left floating leg gathers, the head part is arranged to face outward and the hanging part is arranged to face inward, and
the hanging parts of the pair of right and left floating leg gathers are connected to each other by being respectively coupled to a connection sheet at the lower end parts thereof.

4. The absorbent article according to claim 3, wherein each of outer surfaces of the hanging parts of the pair of right and left floating leg gathers and the connection sheet is coupled.

5. The absorbent article according to claim 3, wherein each of inner surfaces of the hanging parts of the pair of the right and left floating leg gathers and the connection sheet is coupled.

6. The absorbent article according to claim 3, wherein a length in the front-rear direction of the connection sheet is longer than a width in the lateral direction of the connection sheet.

7. The absorbent article according to claim 3, wherein a length in the front-rear direction of the connection sheet is equal to or less than a width in the lateral direction of the connection sheet.

8. The absorbent article according to claim 3, wherein a width in the lateral direction of the connection sheet narrows down from a front side to a rear side.

9. The absorbent article according to claim 3, wherein right and left edge parts of the connection sheet are folded back inwardly on an upper side.

10. The absorbent article according to claim 3, wherein right and left edge parts of the connection sheet are folded back inwardly on an upper side and inwardly-folded-back parts are further folded back outwardly.

11. The absorbent article according to claim 3, wherein the connection sheet is configured by a hydrophilic material.

12. The absorbent article according to claim 3, wherein the connection sheet is configured by a hydrophobic material.

13. The absorbent article according to claim 3, wherein the connection sheet is configured by a combination of a hydrophilic material and a hydrophobic material.

14. The absorbent article according to claim 3, wherein the connection sheet is configured by a material in which hydrophilicity and hydrophobicity are compounded.

15. The absorbent article according to claim 3, wherein the connection sheet is provided beyond a front end and/or a rear end of parts of the hanging parts of the pair of right and left floating leg gathers, which form the transferring passage for bodily fluids.

16. The absorbent article according to claim 3, wherein a transferring direction of the bodily fluid is defined by the transferring passage for bodily fluids having a height difference in the front-rear direction.

17. The absorbent article according to claim 16, wherein the height difference in the transferring passage for bodily fluids is provided due to the existence of a plurality of positions in the vertical direction for coupling the hanging parts of the pair of right and left floating leg gathers to the connection sheet, along the front-rear direction.

18. The absorbent article according to claim 1, wherein, for each of the pair of right and left floating leg gathers, the head part is arranged to face outward and the hanging part is arranged to face inward; and the hanging parts of the pair of right and left floating leg gathers are connected to each other by being respectively directly coupled to each other in the vicinity of the lower end parts thereof.

19. The absorbent article according to claim 1, wherein a member configuring the transferring passage for bodily fluids and the surface of the absorber are spaced apart.

20. The absorbent article according to claim 1, wherein a member configuring the transferring passage for bodily fluids and the surface of the absorber are coupled to each other.

21. The absorbent article according to claim 20, wherein a member configuring the transferring passage for bodily fluids couples to the surface of the absorber in the vicinity of a front end and/or a rear end of the transferring passage for bodily fluids, and the transferring passage for bodily fluids has a fixed part of which height is low and a non-fixed part of which height is high.

22. The absorbent article according to claim 1, wherein the transferring passage for bodily fluids is provided at least in a region of a crotch part.

23. The absorbent article according to claim 1, wherein the transferring passage for bodily fluids is provided at least in a region of a front body.

24. The absorbent article according to claim 1, wherein the transferring passage for bodily fluids is provided at least in a region of a rear body.

25. The absorbent article according to claim 1, wherein at least parts of the hanging parts of the pair of right and left floating leg gathers are connected to each other in a central region of the absorbent article in the vicinity of lower end parts thereof.

26. An absorbent article including:
a leak preventer in sheet form;
an absorber capable of absorbing a bodily fluid, wherein at least one layer thereof is arranged above the leak preventer; and
a pair of right and left floating leg gathers, in which the right floating leg gather is disposed on a right side of the absorbent article and the left floating leg gather is disposed on a left side of the absorbent article, the pair of right and left floating leg gathers are arranged, above the absorber, from a front end part to a rear end part in a length direction of a body of the absorbent article via a front body, a crotch part and a rear body;
wherein the floating leg gather has a head part and a hanging part that connects to the head part,
wherein a front end part and a rear end part of the floating leg gather respectively couple to the vicinity of the front end part and the rear end part of the body of the absorbent article, the hanging part being configured to hang down from the head part toward the absorber,
wherein the hanging part is not connected to a surface of the absorber or the hanging part has a part that is not connected to a surface of the absorber and a part that is connected to the surface of the absorber,
wherein at least parts of the hanging parts of the pair of right and left floating leg gathers are connected to each other above the absorber in the vicinity of lower end parts thereof such that an inner surface side of each of the hanging parts face each other to form a transferring passage for bodily fluids,
wherein for each of the pair of right and left floating leg gathers, the head part is arranged to face outward and the hanging part is arranged to face inward, and the hanging parts of the pair of right and left floating leg gathers are connected to each other by being respectively coupled to a connection sheet at the lower end parts thereof, and
wherein a width in the lateral direction of the connection sheet narrows down from a front side to a rear side.

* * * * *